(12) United States Patent
Matheny

(10) Patent No.: US 12,029,645 B2
(45) Date of Patent: Jul. 9, 2024

(54) METHODS FOR REPLACING DYSFUNCTIONAL HEART VALVES

(71) Applicant: CorMatrix Cardiovascular, Inc., Roswell, GA (US)

(72) Inventor: Robert G Matheny, Norcross, GA (US)

(73) Assignee: Cormatrix Cardiovascular, Inc., Roswell, GA (US)

( * ) Notice: Subject to any disclaimer, the term of this patent is extended or adjusted under 35 U.S.C. 154(b) by 752 days.

(21) Appl. No.: 17/234,266

(22) Filed: Apr. 19, 2021

(65) Prior Publication Data

US 2021/0236278 A1 Aug. 5, 2021

Related U.S. Application Data

(63) Continuation-in-part of application No. 17/233,890, filed on Apr. 19, 2021, which is a continuation-in-part of application No. 17/177,359, filed on Feb. 17, 2021, and a continuation-in-part of application No. 16/129,968, filed on Sep. 13, 2018, now Pat. No. 10,952,843, which is a continuation-in-part of application No. 15/206,833, filed on Jul. 11, 2016, now Pat. No. 10,188,510, and a continuation-in-part of application No. 14/960,354, filed on Dec. 5, 2015, now Pat. No. 9,907,649, and a continuation-in-part of application No. 14/229,854, filed on Mar. 29, 2014, now Pat. No. 9,308,084.

(51) Int. Cl.
| | |
|---|---|
| A61F 2/24 | (2006.01) |
| A61L 27/36 | (2006.01) |
| A61L 27/54 | (2006.01) |
| A61L 31/08 | (2006.01) |
| A61L 31/14 | (2006.01) |
| A61F 2/95 | (2013.01) |

(52) U.S. Cl.
CPC .......... *A61F 2/2418* (2013.01); *A61F 2/2436* (2013.01); *A61L 27/3604* (2013.01); *A61L 27/54* (2013.01); *A61L 31/08* (2013.01); *A61L 31/14* (2013.01); *A61F 2/9522* (2020.05); *A61F 2220/0016* (2013.01); *A61L 27/3629* (2013.01); *A61L 2300/406* (2013.01); *A61L 2430/20* (2013.01)

(58) Field of Classification Search
None
See application file for complete search history.

(56) References Cited

U.S. PATENT DOCUMENTS

| | | | |
|---|---|---|---|
| 2013/0190860 A1 | 7/2013 | Sundt, III | |
| 2018/0078370 A1* | 3/2018 | Kovalsky | ............... A61F 2/2433 |
| 2020/0022808 A1* | 1/2020 | Matheny | ............... A61F 2/2412 |

* cited by examiner

*Primary Examiner* — Megan Y Wolf
(74) *Attorney, Agent, or Firm* — Thomas | Horstemeyer, LLP

(57) ABSTRACT

A percutaneous transcatheter valve delivery method for replacing a dysfunctional heart valve; particularly, an atrio-ventricular (AV) valve, with a prosthetic valve comprising a base valve structure and a stent structure. The transcatheter implantation method accurately positions and securely engages the prosthetic valve in a valve annulus region.

13 Claims, 15 Drawing Sheets

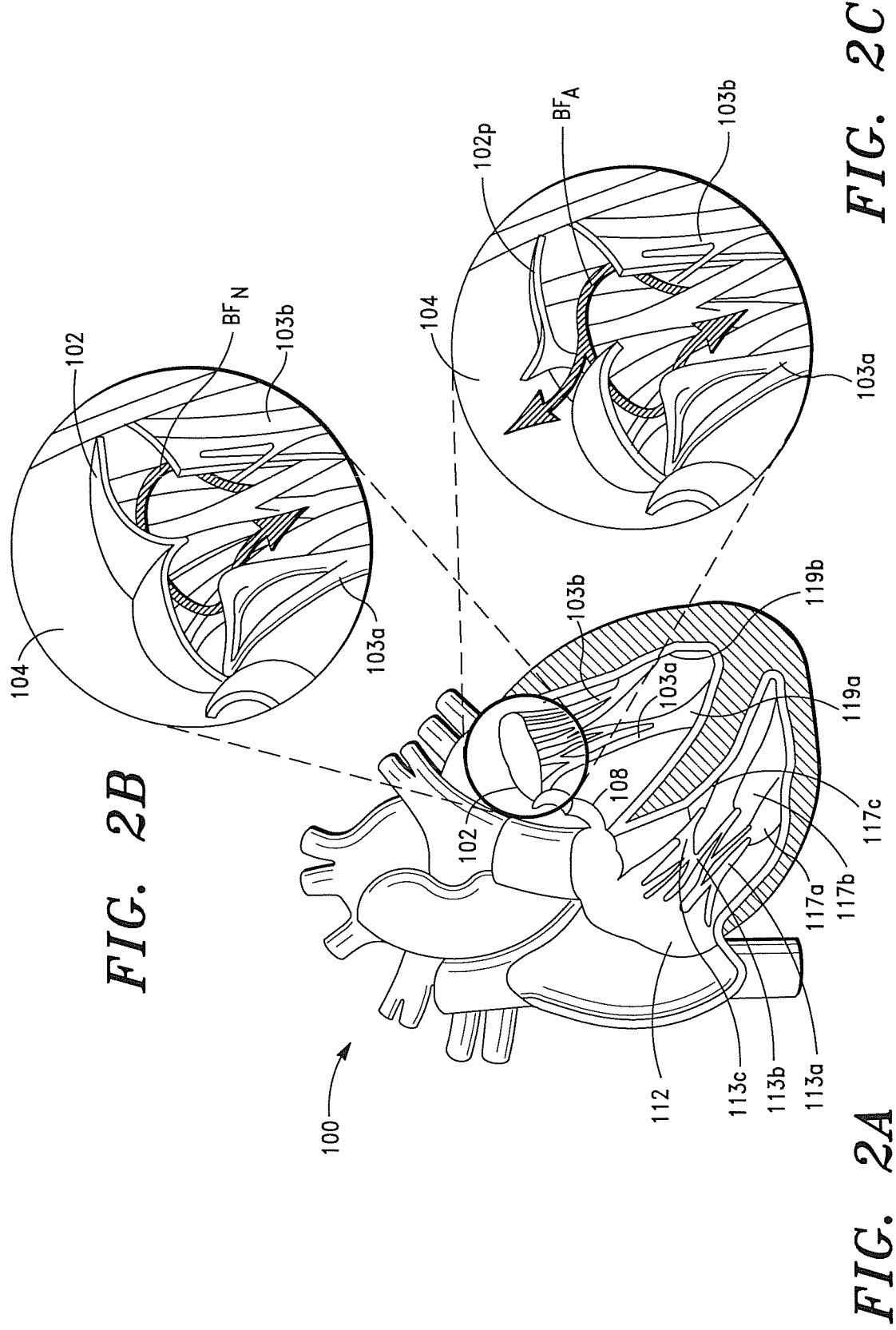

METHODS FOR REPLACING DYSFUNCTIONAL HEART VALVES

CROSS-REFERENCE TO RELATED APPLICATIONS

This application is a continuation-in-part of U.S. application Ser. No. 17/233,890, filed on Apr. 19, 2021, which is a continuation-in-part of U.S. application Ser. No. 17/177,359, filed on Feb. 17, 2021, which is a continuation-in-part of U.S. application Ser. No. 16/129,968, filed on Sep. 13, 2018, now U.S. Pat. No. 10,952,843, which is a continuation-in-part of U.S. application Ser. No. 15/206,833, filed on Jul. 11, 2016, now U.S. Pat. No. 10,188,510, which is a continuation-in-part application of U.S. application Ser. No. 14/960,354, filed on Dec. 5, 2015, now U.S. Pat. No. 9,907,649, which is a continuation-in-part application of U.S. application Ser. No. 14/229,854, filed on Mar. 29, 2014, now U.S. Pat. No. 9,308,084, which claims priority to U.S. Provisional Application No. 61/819,232, filed on May 3, 2013.

FIELD OF THE INVENTION

The present invention generally relates to methods for replacing dysfunctional heart valves. More particularly, the present invention relates to improved percutaneous methods for replacing native dysfunctional atrioventricular (AV) valves.

BACKGROUND OF THE INVENTION

As is well known in the art, the human heart has four heart valves that control blood flow circulating through the human body. Referring to FIGS. 1A and 1B, on the left side of the heart 100 is the mitral valve 102, located between the left atrium 104 and the left ventricle 106, and the aortic valve 108, located between the left ventricle 106 and the aorta 110. Both of these valves direct oxygenated blood from the lungs into the aorta 110 for distribution through the body.

The tricuspid valve 112, located between the right atrium 114 and the right ventricle 116, and the pulmonary valve 118, located between the right ventricle 116 and the pulmonary artery 120, however, are situated on the right side of the heart 100 and direct deoxygenated blood from the body to the lungs.

Referring now to FIG. 2A, there are also generally five papillary muscles in the heart 100. The anterior, posterior and septal papillary muscles 117a, 117b, 117c, which are in the right ventricle 116, attach via chordae tendineae 113a, 113b, 113c to the tricuspid valve 112. The anterior and posterior papillary muscles 119a, 119b, which are in the left ventricle 106, attach via chordae tendineae 103a, 103b to the mitral valve 102.

Since heart valves are passive structures that simply open and close in response to differential pressures, the issues that can develop with valves are typically classified into two categories: (i) stenosis, in which a valve does not open properly, and (ii) insufficiency (also called regurgitation), in which a valve does not close properly.

Stenosis and insufficiency can occur as a result of several abnormalities, including damage or severance of one or more chordae or several disease states. Stenosis and insufficiency can also occur concomitantly in the same valve or in different valves.

Both of the noted valve abnormalities can adversely affect organ function and result in heart failure. By way of example, referring first to FIG. 2B, there is shown normal blood flow (denoted "BFN") proximate the mitral valve 102 during closure.

Referring now to FIG. 2C, there is shown abnormal blood flow (denoted "$BF_A$") or regurgitation caused by a prolapsed mitral valve 102p. As illustrated in FIG. 2C, the regurgitated blood "$BF_A$" flows back into the left atrium, which can, if severe, result in heart failure.

In addition to stenosis and insufficiency of a heart valve, surgical intervention may also be required for certain types of bacterial or fungal infections, wherein the valve may continue to function normally, but nevertheless harbors an overgrowth of bacteria (i.e., "vegetation") on the valve leaflets. The vegetation can, and in many instances will, flake off (i.e., "embolize") and lodge downstream in a vital artery.

If such vegetation is present on the valves of the left side (i.e., the systemic circulation side) of the heart, embolization can, and often will, result in sudden loss of the blood supply to the affected body organ and immediate malfunction of that organ. The organ most commonly affected by such embolization is the brain, in which case the patient can, and in many instances will, suffer a stroke.

Likewise, bacterial or fungal vegetation on the tricuspid valve can embolize to the lungs. The noted embolization can, and in many instances will, result in lung dysfunction.

Treatment of the noted heart valve dysfunctions typically comprises reparation of the diseased heart valve with preservation of the patient's own valve or replacement of the valve with a mechanical or bioprosthetic valve, i.e., a prosthetic valve.

Various prosthetic heart valves have thus been developed for replacement of dysfunctional native heart valves. The selection of a particular type of replacement valve depends on many factors, such as the location of the dysfunctional native valve, the age and physiological characteristics of the recipient of the replacement heart valve, and the surgeon's experiences and preferences.

Commonly used replacement heart valves are typically classified in the following three groups: (i) mechanical valves, (ii) allograft tissue valves, and (iii) xenograft tissue valves. Each of the noted valves and disadvantages associated with same are discussed in detail below.

Mechanical Heart Valves

As is well known in the art, mechanical heart valves, such as caged-ball valves, bi-leaflet valves, and tilting disk valves, typically comprise various metal and polymeric components, which can, and in most instances will, induce an adverse inflammatory response when implanted in a patient or subject.

A further disadvantage associated with mechanical heart valves is that such valves also have a propensity to cause the formation of blood clots after implantation in a patient. If such blood clots form on the mechanical valve, they can preclude the valve from opening or closing correctly or, more importantly, can disengage from the valve and embolize to the brain, causing an embolic stroke. Thus, recipients of a mechanical heart valve are typically required to take systemic anticoagulant drugs for the rest of their lives. In addition to being expensive, these anticoagulant drugs can themselves be dangerous in that they can cause abnormal bleeding in the recipient or patient that can lead to a hemorrhagic stroke.

A further disadvantage associated with mechanical heart valves is that such valves are notoriously difficult to implant and often require large and cumbersome catheter assemblies for percutaneous or transapical implantation. These large catheter assemblies are excessively difficult to operate during a percutaneous or transapical implantation procedure.

Allograft Tissue Valves

As is also well known in the art, allograft tissue valves are harvested from human sources, such as human cadavers. Unlike mechanical heart valves, allograft tissue valves typically do not promote blood clot formation and, therefore, avoid the need for prescribing an anticoagulant medication for the recipient or patient. However, there are still several drawbacks and disadvantages associated with allograft tissue valves.

A major disadvantage associated with allograft tissue valves is that such valves are not available in sufficient numbers to satisfy the needs of all patients who need new heart valves.

A further major disadvantage associated with allograft tissue valves is that recipients of allograft tissue valves, i.e., patients, are typically required to take systemic antirejection and/or immunosuppressive drugs for a predetermined period of time and, in some instances, for a lifetime. Although antirejection and/or immunosuppressive drugs increase the possibility that a patient will accept an allograft without complications, the drugs will often leave the recipient vulnerable to a plurality of other infectious diseases, including bacterial infections, fungal infections, viral infections and the like.

Xenograft Tissue Valves

As is additionally well known in the art, xenograft tissue valves are formed from non-human tissue sources, such as cows or pigs. Xenograft tissue valves are similarly less likely to cause blood clot formation than comparable mechanical valves. However, there are also several drawbacks and disadvantages associated with most conventional allograft tissue valves.

A major disadvantage associated with conventional xenograft tissue valves is that such valves often comprise glutaraldehyde processed tissue and, hence, are prone to calcification and lack the long-term durability of mechanical valves.

More recently, remodelable xenograft tissue valves comprising decellularized extracellular matrix (ECM) have been developed and employed to replace native diseased or defective heart valves. Such valves are not prone to calcification and, as set forth in Applicant's U.S. Pat. Nos. 9,308,084, 9,011,526, 8,709,076 and 10,952,843, which are expressly incorporated by reference herein in their entirety, have the capacity to remodel, i.e., form valve structures similar to native valve structures when implanted in a patient, and induce remodeling of native cardiovascular tissue and regeneration of new cardiovascular tissue when implanted in a patient.

Although most remodelable xenograft ECM tissue valves substantially reduce and, in most instances, eliminate the major disadvantages and drawbacks associated with mechanical valves, allograft tissue valves, and conventional xenograft tissue valves, there are several problems that are often encountered by surgeons when replacing dysfunctional native heart valves with a prosthetic heart valve, including mechanical valves, allograft tissue valves, and most xenograft tissue valves (non-remodelable and remodelable), via conventional surgical methods.

Two seminal problems that are often encountered by surgeons when replacing dysfunctional native heart valves with a prosthetic heart valve via conventional surgical methods, including open-heart surgical methods and percutaneous valve delivery methods, are (i) accurate placement of the prosthetic heart valve in a valve annulus region and (ii) obtaining a secure and reliable engagement of the prosthetic heart valve to the valve annulus.

Although accurate placement of a prosthetic heart valve in a valve annulus region is generally achieved by most open-heart surgical methods, there are numerous significant disadvantages and drawbacks associated with open-heart surgery, including, the high risk of infections, cardiac tamponade, long patient recovery times and the time spent on cardiopulmonary bypass during the open-heart surgery, which also increases the probability of post-surgical complications.

Further, obtaining a secure and reliable engagement of the prosthetic heart valve to the valve annulus remains an issue due to several factors, including, the methods employed to attach the prosthetic heart valve to the valve annulus, and, of course, the experience and skill of the surgeon.

Various percutaneous transcatheter, e.g., transvascular, transseptal and transapical, valve delivery systems and methods have thus been developed to (i) accurately deliver and position a prosthetic heart valve in a valve annulus region to replace a dysfunctional native heart valve and (ii) securely and reliably engage the prosthetic heart valve to the valve annulus.

Illustrative are the transseptal valve delivery systems and methods disclosed in Applicant's U.S. Pat. Nos. 10,857,263, 10,952,845 and 10,945,838, the transvascular valve delivery systems and methods disclosed in U.S. Pat. No. 9,023,101 and U.S. Pub. No. 2021/0045874, and the transapical valve delivery systems and methods disclosed in U.S. Pat. Nos. 10,058,313 and 10,500,047.

Although accurate placement of a prosthetic heart valve in a valve annulus region and secure engagement thereof to the valve annulus can be, and often is, achieved via the aforementioned percutaneous transcatheter valve delivery systems and methods, there still remains a few drawbacks and disadvantages associated with the noted percutaneous transcatheter valve delivery systems and methods.

A major drawback is limited in situ control and positioning of the prosthetic heart valve at the valve annulus region during delivery of the valve thereto.

There is thus a need to provide improved percutaneous valve delivery methods for accurately positioning prosthetic heart valves in a valve annulus region during delivery of the valve thereto.

There is also a need to provide improved percutaneous transcatheter valve delivery methods that facilitate secure and reliable engagement of prosthetic heart valves to a valve annulus.

It is therefore an object of the present invention to provide improved percutaneous transcatheter valve delivery methods for accurately positioning prosthetic heart valves in a valve annulus region during delivery of the valve thereto.

It is another object of the present invention to provide improved percutaneous transcatheter valve delivery methods that facilitate secure and reliable engagement of prosthetic heart valves to a valve annulus.

SUMMARY OF THE INVENTION

The present invention is directed to percutaneous transcatheter methods for replacing native dysfunctional heart valves; and, in particular, dysfunctional atrioventricular (AV) valves.

In one preferred embodiment of the invention, the percutaneous transcatheter method for replacing a dysfunctional AV valve generally comprises the following steps:

(i) providing a prosthetic valve comprising a base valve structure and a self-expanding internal stent structure, the prosthetic valve being adapted to be everted to an everted pre-deployment configuration and, thereafter, be compressed to an everted, compressed pre-deployment configuration,
the prosthetic valve being further adapted to transition from the everted, compressed pre-deployment configuration to an everted, expanded post-deployment configuration, and, thereafter, be reverted to a reverted, expanded post-deployment configuration;

(ii) providing a catheter assembly adapted to access to the AV valve annulus region of the dysfunctional AV valve, the catheter assembly preferably comprising a sheath member and a deployment member,
the sheath member being configured and adapted to receive the prosthetic valve therein when the prosthetic valve is in the everted, compressed pre-deployment configuration;

(iii) everting the prosthetic valve to an everted pre-deployment configuration;

(iv) compressing the prosthetic valve to an everted, compressed pre-deployment configuration;

(v) loading the everted, compressed prosthetic valve into the catheter assembly sheath member;

(vi) selecting a vein that provides access to the AV valve annulus region of the dysfunctional AV valve;

(vii) placing an incision through tissue proximate the vein and through the vein, wherein an opening is provided in the vein;

(viii) inserting the catheter assembly sheath member through the incision, into and through the vein and into the subject's heart;

(ix) guiding the catheter assembly sheath member through the subject's heart and into the AV valve annulus region of the dysfunctional AV valve;

(x) slidably translating the everted, compressed prosthetic valve out of the catheter assembly sheath member and into the AV valve annulus region of the dysfunctional AV valve, wherein the prosthetic valve transitions from the everted compressed pre-deployment configuration to the everted, expanded post-deployment configuration, whereby the prosthetic valve is disposed proximate the cardiovascular tissue of the AV valve annulus region of the dysfunctional AV valve;

(xi) reverting the everted, expanded prosthetic valve to a reverted, expanded post-deployment configuration; and (xii) withdrawing the catheter assembly sheath member out of the subject's body.

In some embodiments of the invention, when the everted, compressed prosthetic valve is guided into the AV valve annulus region of the dysfunctional AV valve, the everted, compressed prosthetic valve is disposed over the dysfunctional AV valve.

In a preferred embodiment of the invention, the prosthetic valve comprises a base valve structure and an internal expandable stent structure.

In a preferred embodiment, the base valve structure comprises a conical shaped ribbon structure comprising a plurality of elongated ribbon members, wherein the edge regions of the elongated ribbon members are positioned proximate each other and form a plurality of fluid flow modulating means.

In a preferred embodiment, the base valve structure comprises pericardium tissue.

In a preferred embodiment, the expandable stent structure comprises a plurality of tethers adapted to pierce cardiovascular tissue and engage the base valve structure thereto, whereby, when the everted, compressed prosthetic valve is guided into the AV valve annulus region of the dysfunctional AV valve, the plurality of stent structure tethers pierce into the cardiovascular tissue at the valve annulus region and, thereby, position the everted, expanded prosthetic valve at the desired position at the valve annulus region and securely engage the everted, expanded prosthetic valve thereto.

In a preferred embodiment, the expandable stent structure comprises a superelastic nickel-titanium (Ni—Ti) alloy.

In some embodiments, the expandable stent structure comprises an outer coating.

In some embodiments, the outer coating comprises an extracellular matrix (ECM) composition comprising acellular ECM derived from a mammalian tissue source.

In some embodiments, the ECM composition is in the form of an expandable composition.

In some embodiments, the ECM composition further comprises a pharmacological agent selected from the group consisting of dexamethasone, betamethasone and prednisolone.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 2A is a further schematic illustration of a human heart;

FIG. 2B is an illustration of a normal mitral valve;

FIG. 2C is an illustration of a prolapsed mitral valve;

DETAILED DESCRIPTION OF THE PREFERRED EMBODIMENT

Figure 1A:
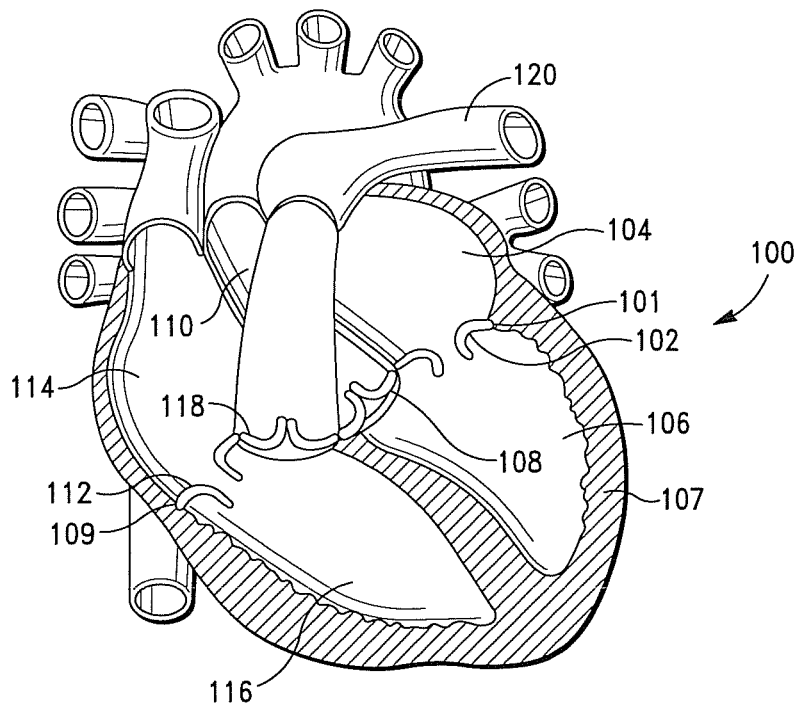
FIGS. 1A and 1B are schematic illustrations of a human heart.
Figure 1B:
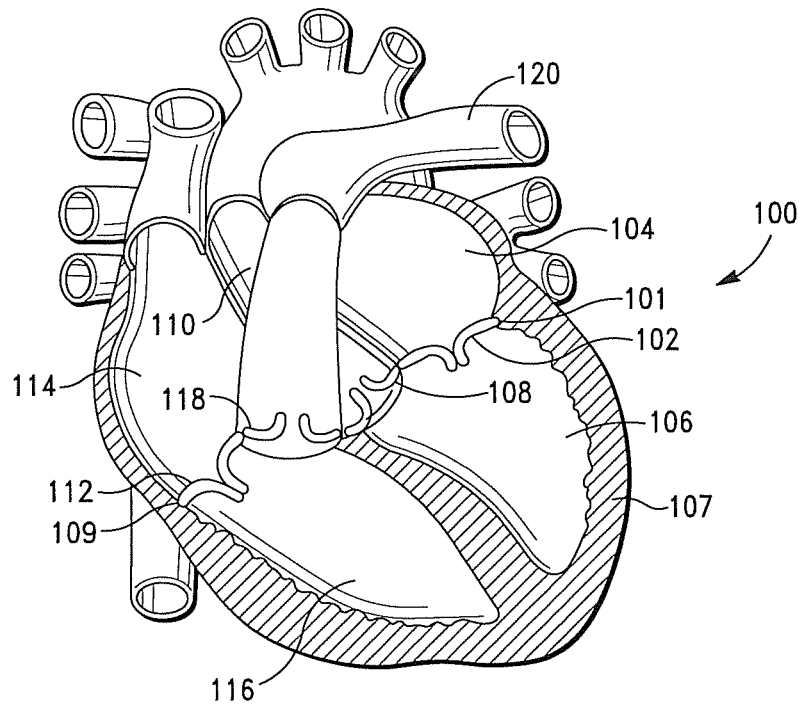

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein are hereby incorporated by reference in their entirety.

As used in this specification and the appended claims, the singular forms "a, "an" and "the" include plural referents unless the content clearly dictates otherwise. Thus, for example, reference to "a pharmacological agent" includes two or more such agents and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed.

It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "extracellular matrix", "ECM", and "ECM material" are used interchangeably herein, and mean and include a collagen-rich substance that is found in between cells in mammalian tissue, and any material processed therefrom, e.g., decellularized ECM.

The term "acellular ECM", as used herein, means ECM that has a reduced content of cells.

According to the invention, ECM can be derived from a variety of mammalian tissue sources and tissue derived therefrom, including, without limitation, small intestine submucosa (SIS), urinary bladder submucosa (UBS), stomach submucosa (SS), central nervous system tissue, epithelium of mesodermal origin, i.e., mesothelial tissue, dermal tissue, subcutaneous tissue, gastrointestinal tissue, tissue surrounding growing bone, placental tissue, omentum tissue, cardiac tissue, kidney tissue, pancreas tissue, lung tissue, and combinations thereof. The ECM can also comprise collagen from mammalian sources.

The terms "heart tissue" and "cardiac tissue" are used collectively herein, and mean and include, without limitation, mammalian tissue derived from any cardiovascular structure including, without limitation, pericardial tissue, myocardial tissue, vascular tissue and the like.

The terms "collagenous mammalian tissue" and "collagenous tissue" are used collectively herein, and mean and include, without limitation, tissue that is also derived from a mammalian tissue source.

According to the invention, the collagenous mammalian tissue can similarly be derived from a variety of mammalian tissue sources and tissue derived therefrom, including, without limitation, the heart, small intestine, large intestine, stomach, lung, liver, kidney, pancreas, peritoneum, placenta, amniotic membrane, umbilical cord, bladder, prostate, and any fetal tissue from any mammalian organ.

The collagenous mammalian tissue can also be derived from a mammalian tissue source that is devoid of xenogeneic antigens, including, without limitation, collagenous mammalian tissue that is devoid of one of the following xenogeneic antigens: galactose-alpha-1,3-galactose (also referred to as α-gal), beta-1,4 N-acetylgalactosaminyltransferase 2, membrane cofactor protein, hepatic lectin H1, cytidine monophospho-N-acetylneuraminic acid hydroxylase, swine leukocyte antigen class I and porcine endogenous retrovirus polymerase (referred to herein as "immune privileged collagenous mammalian tissue").

The term "genetically modified organism", as used herein means and includes any living organism that has at least one gene modified by artificial means, e.g., gene editing.

The term "immune privileged collagenous mammalian tissue", as used herein means and includes xenogeneic collagenous mammalian tissue that can be disposed proximate mammalian tissue with a minimal or virtually absent adverse immune response; particularly, an adverse immune response associated with xenogeneic tissue graft rejection.

According to the invention, the term "mammalian" means and includes, without limitation, warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "crosslinked collagenous mammalian tissue", as used herein, means and includes mammalian tissue that exhibits at least 25% chemical bonding of adjacent chains of molecules, i.e., collagen fibrils, which comprise the collagenous mammalian tissue.

The term "polymer", as used herein means and includes, without limitation, polyurethane urea, porous polyurethane urea (Artelon®), polypropylene, poly(ε-caprolactone) (PCL), poly(glycerol sebacate) (PGS), polytetrafluoroethylene (PTFE), poly(styrene-block-isobutylene-block-Styrene) (SIBS), polyglycolide (PGA), polylactide (PLA), polydioxanone (a polyether-ester), polylactide-co-glycolide, polyamide esters, polyalkalene esters, polyvinyl esters, polyvinyl alcohol, polyanhydrides, polyurethanes, polydimethylsiloxanes, poly(ethylene glycol), polytetrafluoroethylene (Teflon™) and polyethylene terephthalate (Dacron™).

The term "biologically active agent", as used herein, means and includes an agent that induces or modulates a physiological or biological process, or cellular activity, e.g., induces proliferation, and/or growth and/or regeneration of tissue.

The term "biologically active agent" thus means and includes a growth factor, including, without limitation, fibroblast growth factor-2 (FGF-2), transforming growth factor beta (TGF-β) and vascular endothelial growth factor (VEGF).

The term "biologically active agent" also means and includes a cell, including, without limitation, human embryonic stem cells, myofibroblasts, mesenchymal stem cells, and hematopoietic stem cells.

The term "biologically active agent" also means and includes agents commonly referred to as a "protein", "peptide" and "polypeptide", including, without limitation, collagen (types I-V), proteoglycans and glycosaminoglycans (GAGs).

The terms "pharmacological agent", "active agent" and "drug" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent" and "drug" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPs), enzymes and enzyme inhibitors, anticoagulants and/or anti-thrombotic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent" and "drug" also mean and include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti-VEGFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), NT-3, NT-4, NGF and IGF-2.

The terms "pharmacological agent", "active agent" and "drug" also mean and include the Class I-Class V antiarrhythmic agents disclosed in Applicant's U.S. Pat. Nos. 9,119,841, 10,188,509, 10,188,510, 10,143,778 and 10,952,843, and U.S. application Ser. No. 16/990,236, including, without limitation, (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent" and "drug" also mean and include, without limitation, the antibiotics disclosed in Applicant's U.S. Pat. Nos. 9,119,841, 10,188,509, 10,188,510, 10,143,778 and 10,952,843, and U.S. application Ser. No. 16/990,236, including, without limitation, aminoglycosides, cephalosporins, chloramphenicol, clindamycin, erythromycins, fluoroquinolones, macrolides, azolides, metronidazole, penicillin, tetracyclines, trimethoprim-sulfamethoxazole, gentamicin and vancomycin.

As indicated above, the terms "pharmacological agent", "active agent" and "drug" also mean and include an anti-inflammatory.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e., the protective tissue response to injury or destruction of tissues, which serves to destroy, dilute, or wall off both the injurious agent and the injured tissues.

The terms "anti-inflammatory" and "anti-inflammatory agent" thus include the anti-inflammatories disclosed in Applicant's U.S. Pat. Nos. 9,119,841, 10,188,509, 10,188,510, 10,143,778 and 10,952,843, and U.S. application Ser. No. 16/990,236, including, without limitation, desoximetasone, dexamethasone dipropionate, cloticasone propionate, diftalone, fluorometholone acetate, fluquazone, meseclazone, mesterolone, methandrostenolone, methenolone, methenolone acetate, methylprednisolone suleptanate, halopredone acetate, alclometasone dipropionate, apazone, balsalazide disodium, cintazone cormethasone acetate, cortodoxone, diflorasone diacetate, diflumidone sodium, endrysone, fenpipalone, flazalone, fluretofen, fluticasone propionate, isoflupredone acetate, nabumetone, nandrolone, nimazone, oxyphenbutazone, oxymetholone, phenbutazone, pirfenidone, prifelone, proquazone, rimexolone, seclazone, tebufelone and testosterone.

The terms "pharmacological agent", "active agent" and "drug" also mean and include the statins, i.e., HMG-CoA reductase inhibitors, disclosed in Applicant's U.S. Pat. Nos. 9,119,841, 10,188,509, 10,188,510, 10,143,778 and 10,952,843, and U.S. application Ser. No. 16/990,236, including, without limitation, atorvastatin, cerivastatin, fluvastatin and lovastatin.

The terms "pharmacological agent", "active agent", "drug" and "active agent formulation" further mean and include the anti-proliferative agents disclosed in Applicant's U.S. Pat. Nos. 9,119,841, 10,188,509, 10,188,510, 10,143,778 and 10,952,843, and U.S. application Ser. No. 16/990,236, including, without limitation, paclitaxel, sirolimus and derivatives thereof, including everolimus.

The term "pharmacological composition", as used herein, means and includes a composition comprising a "pharmacological agent" and/or any additional agent or component identified herein.

Additional biologically active and pharmacological agents are set forth in priority U.S. application Ser. No. 15/206,833, now U.S. Pat. No. 10,188,510, which is expressly incorporated herein in its entirety.

The term "therapeutically effective", as used herein, means that the amount of the "pharmacological agent" and/or "biologically active agent" and/or "pharmacological composition" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The term "comprise" and variations of the term, such as "comprising" and "comprises," as used in connection with the a prosthetic valve composition and/or mammalian tissue, also means a composition and/or mammalian tissue employed to form a prosthetic valve structure, such as a sheet member, and, hence, a prosthetic valve of the invention.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As stated above, the present invention is directed to percutaneous transcatheter valve delivery methods for replacing dysfunctional, i.e., diseased or defective, AV or heart valves, including, without limitation, tricuspid and mitral valves, with prosthetic heart valves.

More particularly, the present invention is directed to percutaneous transcatheter valve delivery methods for (i) accurately positioning prosthetic heart valves in a valve annulus region and (ii) securely and consistently reliably engaging the prosthetic heart valves to a valve annulus in the valve annulus region.

As will readily be appreciated by one skilled in the art, the percutaneous transcatheter methods of the invention can be readily employed to accurately position most non-mechanical prosthetic heart valves; particularly, prosthetic allograft and xenograft tissue heart valves in a valve annulus region, and securely and consistently reliably engage the prosthetic heart valves thereto.

Thus, although the percutaneous transcatheter valve delivery methods of the invention are often described in connection with replacement of dysfunctional native tricuspid valves, it is to be understood that the methods of the invention are not limited to replacement of dysfunctional native tricuspid valves. Indeed, the methods of the invention can also be readily employed to replace other cardiovascular valves, including mitral valves.

As is well known in the art, the first steps in any method for replacing a defective AV valve with a prosthetic valve are to (i) identify the dysfunctional AV valve requiring replacement with a prosthetic valve and (ii) prepare the AV valve annulus of the dysfunctional AV valve for receipt of the prosthetic valve.

As is also well known in the art, preparing an AV valve annulus for receipt of a prosthetic valve typically comprises excising the dysfunctional AV valve or leaflets thereof.

As will readily be appreciated by one having ordinary skill in the art, one of the many advantages of the methods of the invention described herein is that the prosthetic valves can be implanted in a subject without removing the native dysfunctional AV valve or leaflets thereon.

According to the invention, after the dysfunctional AV valve is identified and the valve annulus region of the dysfunctional AV valve is prepared for receipt of the prosthetic valve, if necessary or desired, as indicated above and discussed in detail below, in one embodiment of the invention, the percutaneous transcatheter method for replacing the dysfunctional AV valve preferably comprises the following steps:

(i) selecting and providing a desired prosthetic valve of the invention and, hence, a prosthetic valve adapted to be everted to an everted pre-deployment configuration and, thereafter, be compressed to an everted, compressed pre-deployment configuration, the prosthetic valve being further adapted to transition from the everted, compressed pre-deployment configuration to an everted, expanded post-deployment configuration, and, thereafter, be reverted to a reverted, expanded post-deployment configuration;

(ii) providing a catheter assembly adapted to access the AV valve annulus region of the dysfunctional AV valve, the catheter assembly preferably comprising a sheath member and a deployment member, the sheath member being configured and adapted to receive the prosthetic valve therein when the prosthetic valve is in the everted, compressed pre-deployment configuration;

(iii) everting the prosthetic valve to the everted pre-deployment configuration;

(iv) compressing the prosthetic valve to the everted, compressed pre-deployment configuration;

(v) loading the everted, compressed prosthetic valve into the catheter assembly sheath member;

(vi) selecting a vein that provides access to the AV valve annulus region of the dysfunctional AV valve;

(vii) placing an incision through tissue proximate the vein and through the vein, wherein an opening is provided in the vein;

(viii) inserting the catheter assembly sheath member through the incision, into and through the vein and into the subject's heart;

(ix) guiding the catheter assembly sheath member through the subject's heart and into the valve annulus region of the dysfunctional AV valve;

(x) slidably translating the everted, compressed prosthetic valve out of the catheter assembly sheath member and into the AV valve annulus region of the dysfunctional AV valve, wherein the prosthetic valve transitions from the everted compressed pre-deployment configuration to an everted, expanded post-deployment configuration, whereby the prosthetic valve is disposed proximate the cardiovascular tissue of the AV valve annulus region of the dysfunctional AV valve;

(xi) reverting the everted, expanded prosthetic valve to a reverted, expanded post-deployment configuration; and (xii) withdrawing the catheter assembly sheath member out of the subject's heart and out of the subject's body.

As indicated above, in a preferred embodiment, the prosthetic valve comprises a base valve structure and an internal expandable stent structure, such as the preferred prosthetic valves disclosed in Applicant's Co-pending U.S. application Ser. No. 17/233,890, which is expressly incorporated by reference herein, As set forth in Applicant's Co-pending U.S. application Ser. No. 17/233,890, the base valve structure preferably comprises a continuous conical shaped structural member having a plurality of flow modulation means.

According to the invention, in one preferred embodiment, the conical shaped structural member comprises a conical shaped ribbon structure having a plurality of elongated ribbon members, wherein the edge regions of the elongated ribbon members are positioned proximate each other and form the plurality of fluid flow modulating means.

In some embodiments, the conical shaped structural member comprises a conical shaped sheet structure comprising a plurality of linear interstices, which form the plurality of fluid flow modulating means.

As also set forth in Applicant's Co-pending U.S. application Ser. No. 17/233,890, the base valve structure can comprise and, hence, be formed with various biocompatible materials and compositions.

Preferably, the base valve structure comprises collagenous tissue from a mammalian tissue source.

As further set forth in Applicant's Co-pending U.S. application Ser. No. 17/233,890, suitable mammalian tissue sources, include, without limitation, the heart, small intestine, large intestine, stomach, lung, liver, kidney, pancreas, peritoneum, placenta, amniotic membrane, umbilical cord, bladder, prostate, and any fetal tissue from any mammalian organ.

In a preferred embodiment, the mammalian tissue source comprises heart tissue; specifically, pericardium tissue.

As additionally set forth in Applicant's Co-pending U.S. application Ser. No. 17/233,890, the pericardium tissue can comprise at least one additional biologically active agent or composition and/or at least one pharmacological agent or composition (or drug), i.e., an agent or composition that is capable of producing a desired biological effect in vivo, e.g., stimulation or suppression of apoptosis, stimulation or suppression of an immune response, etc., such as, without limitation, one of the aforementioned biologically active agents, including, without limitation, the aforementioned growth factors, cells and proteins, and pharmacological agents, including, without limitation, the aforementioned antibiotics and anti-inflammatories.

As also indicated above, in a preferred embodiment, the prosthetic valve further comprises an expandable stent structure.

Preferably, the expandable stent structure is configured and adapted to enhance the structural integrity of the base valve structure.

As also indicated above and discussed in detail below, in a preferred embodiment, the expandable stent structure comprises a plurality of tethers adapted to pierce cardiovascular tissue and engage the base valve structure thereto, whereby, when the everted, compressed prosthetic valve is guided into the AV valve annulus region of the dysfunctional AV valve, the plurality of stent structure tethers pierce into the cardiovascular tissue at the AV valve annulus region and, thereby, position the everted, expanded prosthetic valve at the desired position at the AV valve annulus region and securely engage the everted, expanded prosthetic valve thereto.

In a preferred embodiment, the expandable stent structure comprises a shape-memory, i.e., superelastic, Ni—Ti alloy (referred to hereinafter as "Nitinol®").

As further set forth in Applicant's Co-pending U.S. application Ser. No. 17/233,890, the expandable stent structure can further comprise an outer coating comprising one of the aforementioned ECM or polymeric compositions.

Figure 3A:
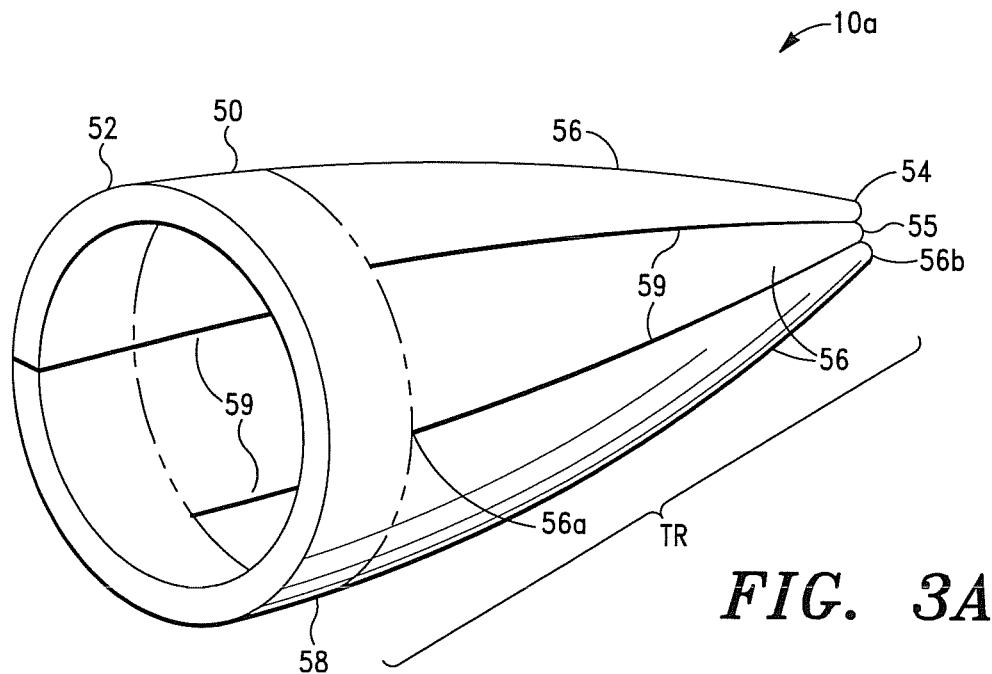
FIG. 3A is a perspective view of one embodiment of a base "ribbon structure" valve structure, in accordance with the invention.
Figure 3B:
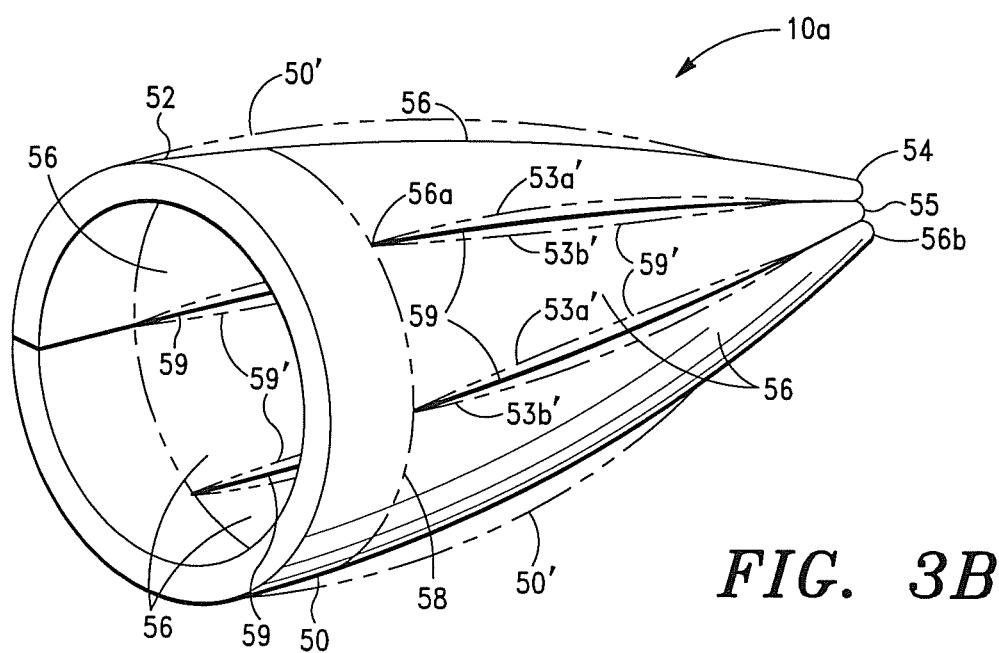
FIG. 3B is a further perspective view of the base "ribbon structure" valve structure shown in FIG. 3A, in accordance with the invention.

Referring now to FIGS. 3A-3B, there is shown one embodiment of a base valve structure of the invention, denoted 10a.

As set forth in Applicant's Co-pending U.S. application Ser. No. 17/233,890 and illustrated in FIGS. 3A and 3B, the base valve structure 10a comprises a ribbon structure comprising a proximal valve annulus engagement end 52 having a circumferential ribbon connection region 58, and a distal end 54. The base member 50 further comprises a plurality of ribbon members or ribbons 56 that are connected to and extend from the ribbon connection region 58.

As further illustrated in FIGS. 3A and 3B, each of the plurality of ribbons 56 preferably comprise proximal and distal ends 56a, 56b, and first and second edge regions 53a, 53b that extend from the circumferential ribbon connection region 58 to the distal ends 56b of each of the ribbons 56 and, hence, distal end 54 of the base member 50.

The distal ends 56b of the ribbons 56 are also in a joined relationship, wherein blood flow through the joined distal ends 56b of the ribbons 56 is restricted.

As further illustrated in FIG. 3B, the proximal ends 56a of ribbons 56 are positioned circumferentially about the circumferential ribbon connection region 58 of the base member 50, wherein the first edge regions 53a and the second edge regions 53b of the ribbons 56 are positioned adjacent each other and form a plurality of fluid flow modulating regions 59.

As also set forth in Applicant's Co-pending U.S. application Ser. No. 17/233,890 and illustrated in FIG. 3B, when the base member 50 is engaged to an AV valve annulus, such as a tricuspid valve annulus, and receives blood therein that exhibits a first positive fluid pressure, whereby there is a first positive pressure differential between first internal valvular pressure (resulting from the first positive fluid pressure) and first external pressure, whereby internal forces are exerted on the internal surface of the base member 50, i.e., taper region thereof (denoted "TR" in FIG. 3A) and, thus, flow modulating regions 59, the base member 50 is adapted to expand to an expanded configuration, whereby the flow modulating regions 59 (i.e., ribbons 56) deflect outwardly to an open or unrestricted fluid flow configuration, as shown in phantom and denoted 50', i.e., the first and second edge regions 53a, 53b separate, as shown in phantom and denoted 53a', 53b', whereby the blood is allowed to be transmitted through and out of the flow modulating regions 59 and, hence, base member 50.

As further illustrated in FIG. 3B, the base member 50 is adapted to transition from the expanded configuration to a contracted configuration, whereby the ribbons 56 deflect inwardly and the flow modulating regions 59 transition from the open fluid flow configuration to a closed or restricted fluid flow configuration during transition of the first positive pressure differential to a second pressure differential between second internal valvular pressure and second external or left ventricle pressure, the second pressure differential being lower than the first positive pressure differential, such as when blood within the base member 50 exhibits a second positive fluid pressure that is less than the first positive fluid pressure, i.e., a reduced positive fluid pressure, or a negative fluid pressure, wherein the blood through and out of the flow modulating regions 59 and, hence, base member 50 is restricted.

Figure 4A:
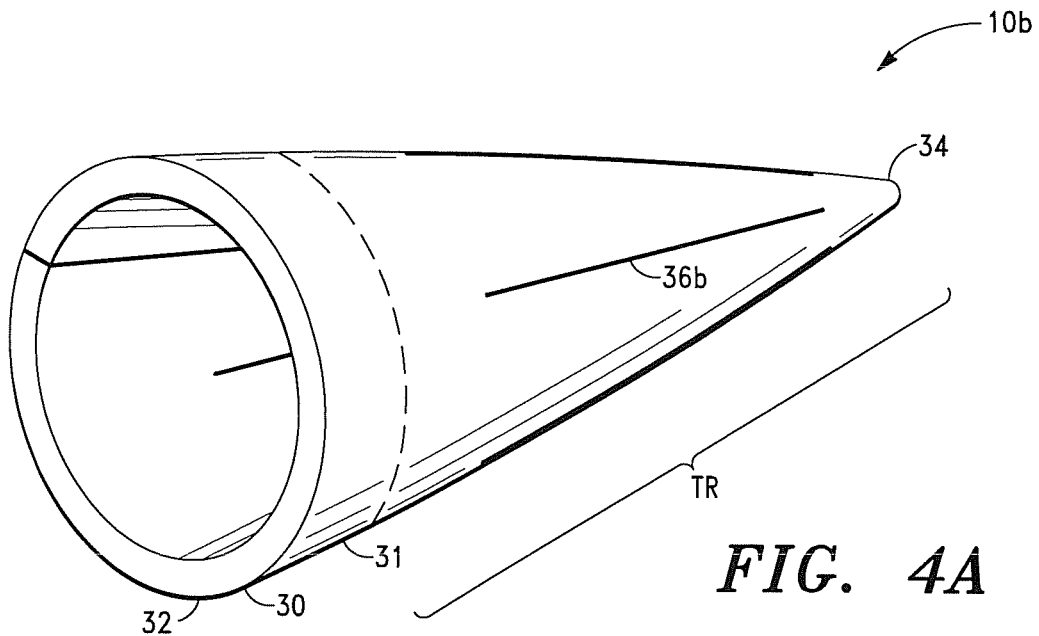
FIG. 4A is a perspective view of one embodiment of a base "sheet structure" valve structure, in accordance with the invention.
Figure 4B:
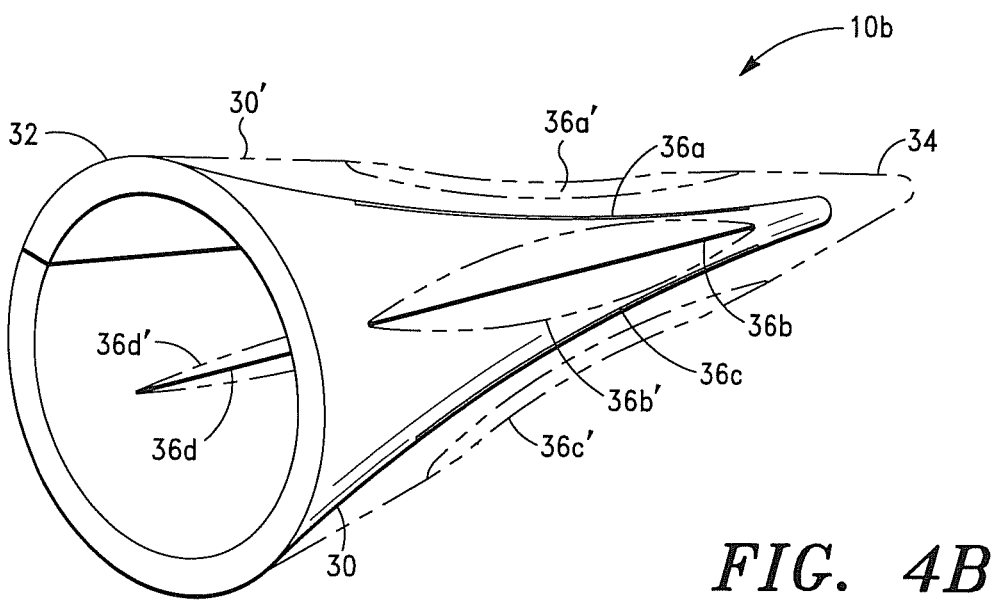
FIG. 4B is a further perspective view of the base "sheet structure" valve structure shown in FIG. 4A, in accordance with the invention.

Referring now to FIGS. 4A-4B, there is shown another embodiment of a base valve structure of the invention, denoted 10b.

As set forth in Applicant's Co-pending U.S. application Ser. No. 17/233,890 and illustrated in FIGS. 4A and 4B, the base valve structure 10b comprises a base sheet member 30 comprising a proximal valve annulus engagement end 32 and distal end 34, and a plurality of flow modulation means, i.e., open regions or interstices, 36a-36d that are preferably disposed linearly over a portion of the length of the base sheet member 30.

As also set forth in Applicant's Co-pending U.S. application Ser. No. 17/233,890, when the base sheet member 30 is engaged to an AV valve annulus, such as a tricuspid valve annulus, and receives blood flow therein that exhibits a first positive fluid pressure, whereby a first positive pressure differential between first internal valvular pressure (resulting from the first positive fluid pressure) and first external pressure is generated and internal forces are exerted on the internal surface of the base sheet member 30, i.e., taper region thereof (denoted "TR" in FIG. 4A), the base sheet member 30 is similarly adapted to expand (i.e., deflect outwardly) to an expanded configuration, as shown in phantom and denoted 30' in FIG. 4B, and transition from the expanded configuration to a contracted configuration during transition of the first positive pressure differential to a second pressure differential between second internal valvular pressure and second external or left ventricle pressure, the second pressure differential being lower than the first positive pressure differential, such as when the blood within base sheet member 30 exhibits a second positive fluid pressure that is less than the first positive fluid pressure, i.e., a reduced positive fluid pressure or a negative fluid pressure.

The interstices 36a-36d are configured and adapted to open to an open or unrestricted configuration during the noted expansion of the base sheet member 30' (denoted 36a', 36b', 36c' and 36d'), wherein the blood is allowed to be transmitted through the interstices 36a', 36b', 36c', 36d' and out of the base sheet member 30', and transition from the open or unrestricted configuration to a restricted or closed configuration during the noted transition of the base sheet member 30' from the expanded configuration to the contracted configuration 30, wherein the blood through and out of the base sheet member 30 is restricted.

As further set forth in Applicant's Co-pending U.S. application Ser. No. 17/233,890, in some embodiments, it is contemplated that, following placement of a prosthetic valve described herein and/or in Applicant's Co-pending U.S. application Ser. No. 17/233,890 on or in a cardiovascular structure (or structures) in a subject, such as an AV valve annulus region, and, hence, cardiovascular tissue associated therewith, the prosthetic valve will induce "modulated healing" of the cardiovascular structure(s) and cardiovascular tissue associated therewith, including, without limitation, modulation of inflammation, i.e., delaying and/or reducing an inflammatory phase restricting the expression of inflammatory components, etc., and inducing host tissue proliferation, remodeling of the cardiovascular tissue and regeneration of new tissue and tissue structures.

According to the invention, the prosthetic valves of the invention can comprise various expandable stent structures that are adapted to enhance the structural integrity of the base valve structure and, hence, prosthetic valves formed therewith.

Figure 5A:
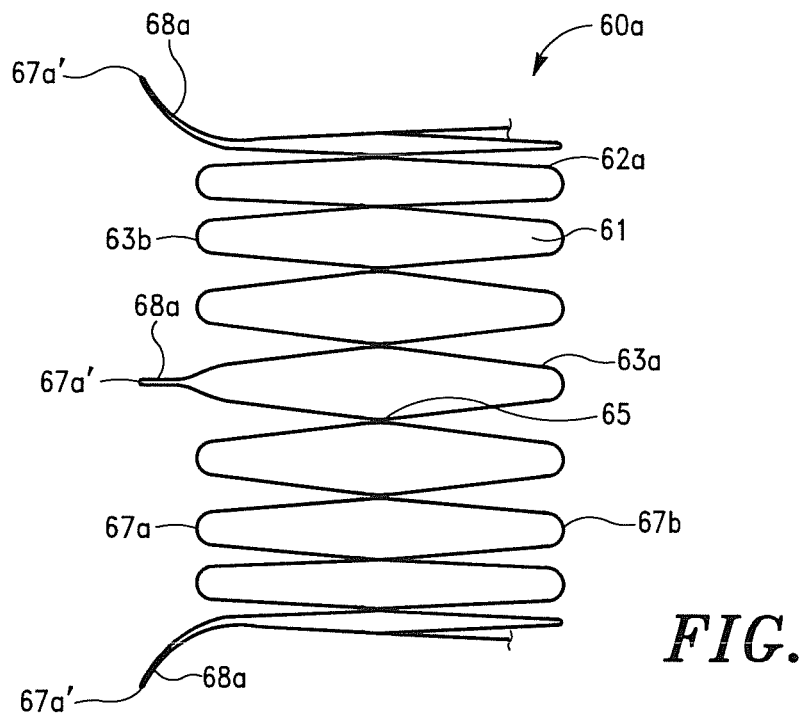
FIG. 5A is a partial side plan view of one embodiment of an expandable stent structure, in accordance with the invention.
Figure 5B:
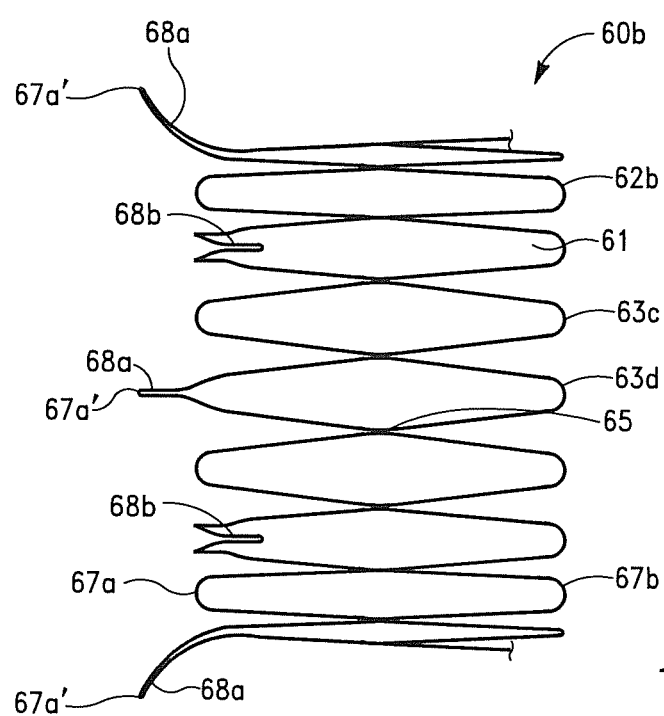
FIG. 5B is a partial side plan view of another embodiment of an expandable stent structure, in accordance with the invention.
Figure 7:
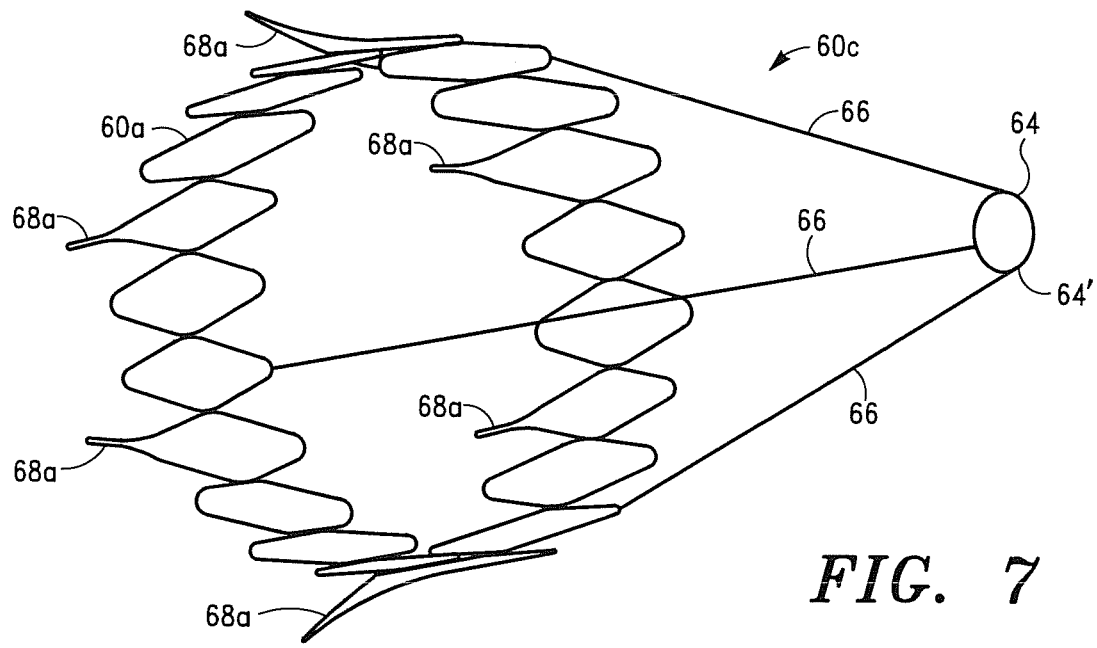
FIG. 7 is a perspective view of another embodiment of an expandable stent structure, in accordance with the invention.

Referring now to FIGS. 5A, 5B and 7, there are shown several embodiments of preferred expandable stent structures that can readily be employed in the prosthetic valves of the invention.

The expandable stent structures, which are described in detail in Applicant's Co-pending U.S. application Ser. No. 17/233,890, are adapted to (i) enhance the structural integrity of the base valve structures and, hence, prosthetic valves formed therewith, (ii) evert, revert, compress and expand, and (iii) facilitate eversion, reversion, compression and expansion of the base valve structure and, hence, prosthetic valve formed therewith when disposed therein.

As illustrated in FIG. 5A, in one embodiment, the expandable stent structure 60a comprises a cross-linked wire structure 62a comprising two (2) band elements 63a, 63b that form a substantially tubular configuration comprising a plurality of substantially uniform rhombus shaped interconnecting cells 61 having proximal and distal ends 67a, 67b.

As further illustrated in FIG. 5A, the interconnecting cells 61 are preferably in communication at points 65.

Figure 6A:
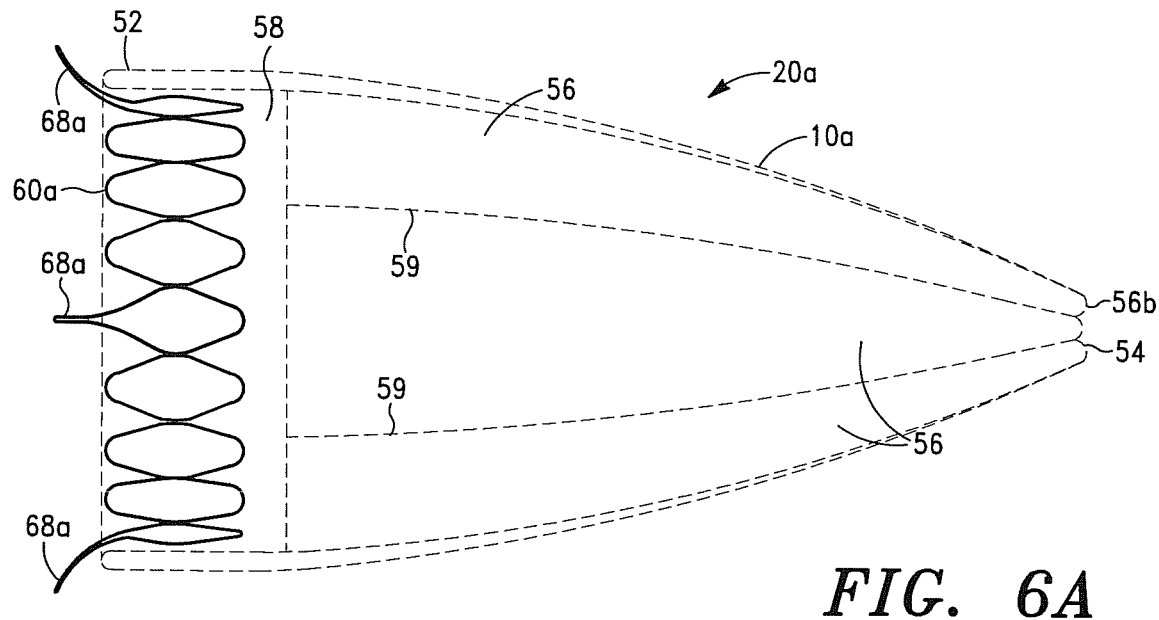
FIG. 6A is a side plan partial sectional view of one embodiment of a prosthetic valve comprising the base valve structure shown in FIG. 3A and the stent structure shown in FIG. 5A, in accordance with the invention.
Figure 6B:
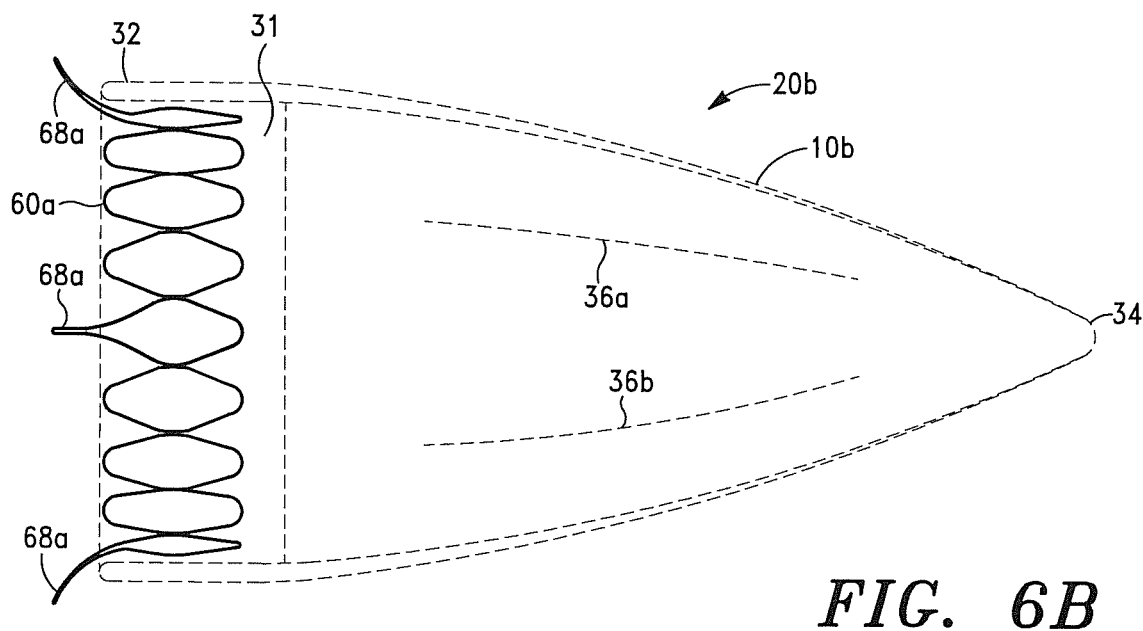
FIG. 6B is a side plan partial sectional view of another embodiment of a prosthetic valve comprising the base valve structure shown in FIG. 4A and the stent structure shown in FIG. 5A, in accordance with the invention.

As set forth in Applicant's Co-pending U.S. application Ser. No. 17/233,890, the cross-linked wire structure 62a (and cross-linked wire structure 62b, discussed below) is adapted to be compressed to a reduced size (i.e., diameter) tubular configuration and transition from the reduced size tubular configuration to an expanded post-deployment configuration (via stent material properties or an internal radial force), such as shown in FIGS. 6A and 6B.

As further illustrated in FIG. 5A, the expandable stent structure 60a further comprises a plurality of positioning and anchoring tethers 68a having a pointed end region 67a', which are positioned, configured and adapted to pierce cardiovascular tissue and, thereby, position the expandable stent structure 60a (and hence, prosthetic valve formed therewith) at a desired valve annulus region and, in some embodiments, secure the prosthetic valve thereto during delivery of the prosthetic valve to the valve annulus region.

Referring now to FIG. 5B, there is shown another embodiment of an expandable stent structure, which can readily be employed in the prosthetic valves of the invention.

As illustrated in FIG. 5B, the expandable stent structure 60b similarly comprises a cross-linked wire structure (in this embodiment, denoted "62b") comprising two (2) band elements 63c, 63d, which similarly form a substantially tubular configuration comprising a plurality of substantially uniform rhombus shaped interconnecting cells 61 having proximal and distal ends 67a, 67b.

However, as illustrated in FIG. 5B, in this embodiment, the expandable stent structure 60b further comprises positioning and anchoring tethers that alternate in opposing directions, i.e., tethers 68a that extend proximally and tethers 68b that extend distally, to position prosthetic valves of the invention formed therewith at a desired valve annulus region and secure the prosthetic valves thereto during delivery of the prosthetic valves to the valve annulus region in operative configurations and directions, as shown in FIGS. 6A and 6B, and everted configurations and directions, as discussed in detail below.

Referring now to FIGS. 6A and 6B, there are shown illustrations of prosthetic valves of the invention comprising base valve structure 10a and expandable stent structure 60a, i.e., prosthetic valve 20a, (FIG. 6A) and base valve structure 10b and expandable stent structure 60a, i.e., prosthetic valve 20b (FIG. 6B).

As illustrated in FIGS. 6A and 6B, in a preferred embodiment, the expandable stent structure 60a is disposed proximate the proximal valve annulus engagement ends 52, 32 of base valve structures 10a and 10b, respectively.

As set forth in Applicant's Co-pending U.S. application Ser. No. 17/233,890 and illustrated in FIGS. 6A and 6B, the expandable stent structure 60a, i.e., cross-linked wire structure 62a thereof, is preferably sized and configured to accommodate the operative diameter of the proximal valve annulus engagement ends 52, 32 of base valve structures 10a and 10b, respectively.

As further forth in Applicant's Co-pending U.S. application Ser. No. 17/233,890, the expandable stent structure 60a (and expandable stent structure 60b) can be secured to the proximal valve annulus engagement ends 52, 32 of base valve structures 10a and 10b by various conventional means.

In some embodiments, the expandable stent structure 60a (and expandable stent structure 60b) is secured to the proximal valve annulus engagement ends 52, 32 of base valve structures 10a and 10b, respectively, by bonding the expandable stent structure 60a (and expandable stent structure 60b) thereto with a conventional adhesive.

In some embodiments, the expandable stent structure 60a (and expandable stent structure 60b) is secured to the proximal valve annulus engagement ends 52, 32 of base valve structures 10a and 10b, respectively, by folding the proximal valve annulus engagement ends 52, 32 of base valve structures 10a, 10b inwardly (i.e., in the base valve structure lumen) and securing the proximal valve annulus engagement ends 52, 32 to the inner surface of base valve structures 10a, 10b via sutures.

Referring now to FIG. 7, there is shown another embodiment of an expandable stent structure, which can readily be employed in the prosthetic valves of the invention.

As set forth in Applicant's Co-pending U.S. application Ser. No. 17/233,890 and illustrated in FIG. 7, the expandable stent structure 60c preferably comprises cross-linked wire structure 62a described above, a circumferential distal end region 64 and a plurality of links 66 disposed between and engaged to the cross-linked wire structure 62a and circumferential distal end region 64, whereby the cross-linked wire structure 62a and circumferential distal end region 64 are in communication.

As further illustrated in FIG. 7, the circumferential distal end region 64 preferably comprises a solid, toroidal shaped (i.e., doughnut-shaped) structure.

Figure 8A:
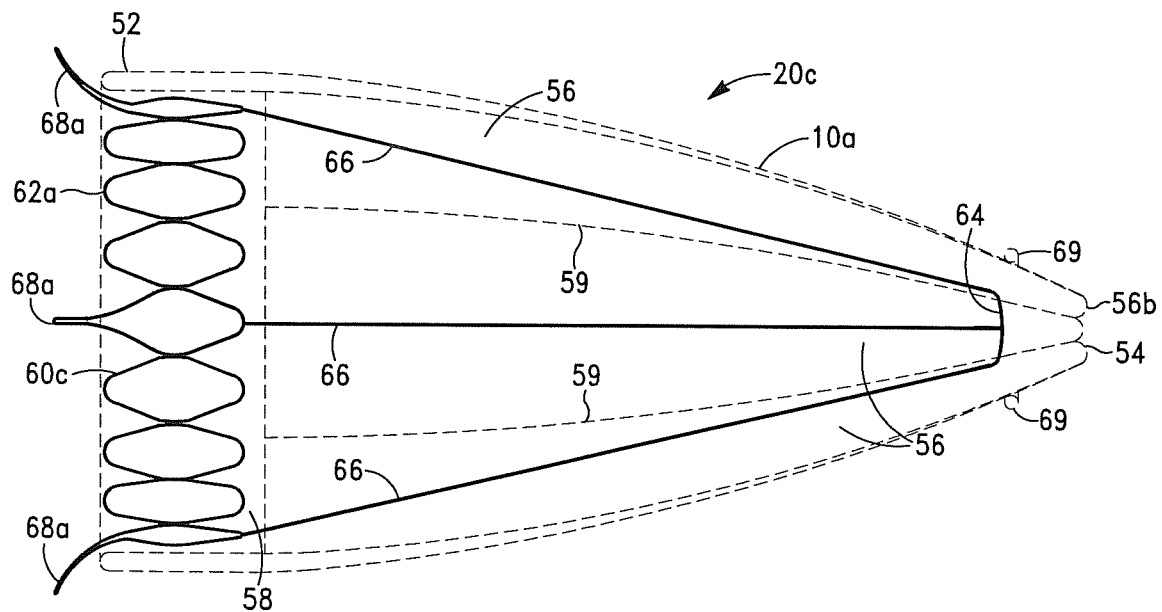
FIG. 8A is a side plan partial sectional view of one embodiment of a prosthetic valve comprising the base valve structure shown in FIG. 3A and the stent structure shown in FIG. 7, in accordance with the invention.
Figure 8B:
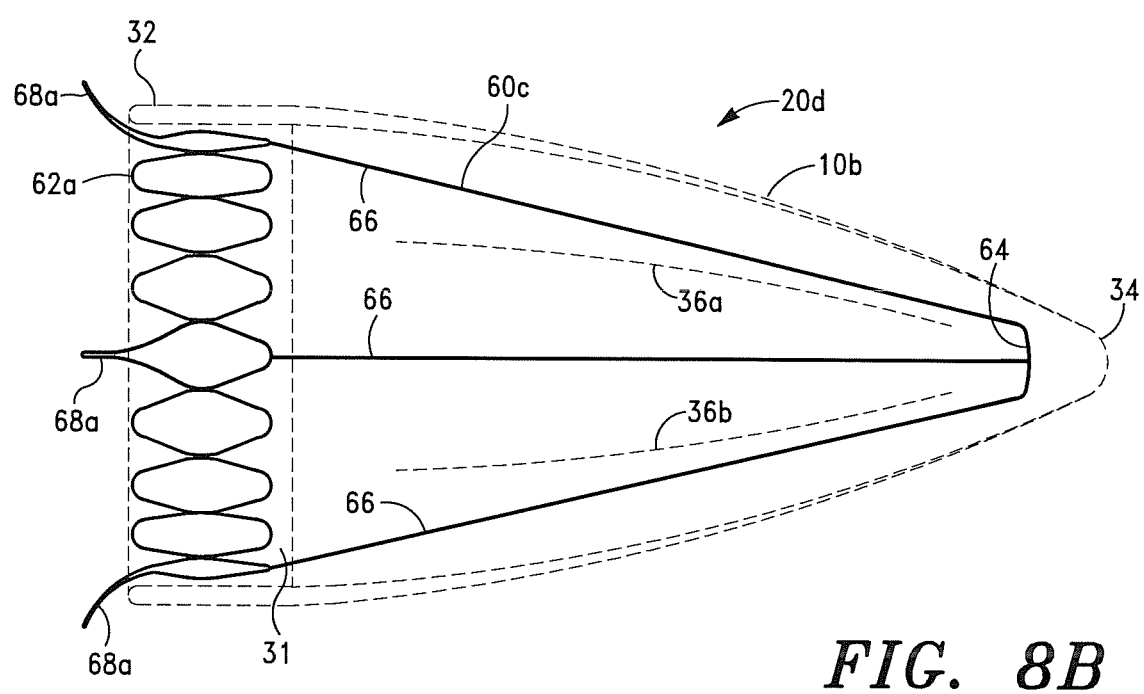
FIG. 8B is a side plan partial sectional view of one embodiment of a prosthetic valve comprising the base valve structure shown in FIG. 4A and the stent structure shown in FIG. 7, in accordance with the invention.

Referring now to FIGS. 8A and 8B, there are shown prosthetic valves of the invention incorporating the base "ribbon structure" valve shown in FIGS. 3A and 3B and the expandable stent structure 60c shown in FIG. 7, denoted 20c (FIG. 8A), and incorporating the base "sheet structure" valve shown in FIGS. 4A and 4B and the expandable stent structure 60c shown in FIG. 7, denoted 20d (FIG. 8B).

As set forth in Applicant's Co-pending U.S. application Ser. No. 17/233,890 and illustrated in FIGS. 8A and 8B, the expandable stent structure 60c, i.e., cross-linked wire structure 62a thereof, is similarly preferably sized and configured to accommodate the operative diameter of the proximal valve annulus engagement ends 52, 32 of base valve structures 10a and 10b, respectively.

As further illustrated in FIGS. 8A and 8B, the circumferential distal end region 64 of the expandable stent structure 60c is also preferably disposed at a predetermined internal distal region of the base valve structures 10a, 10b.

Figure 9:
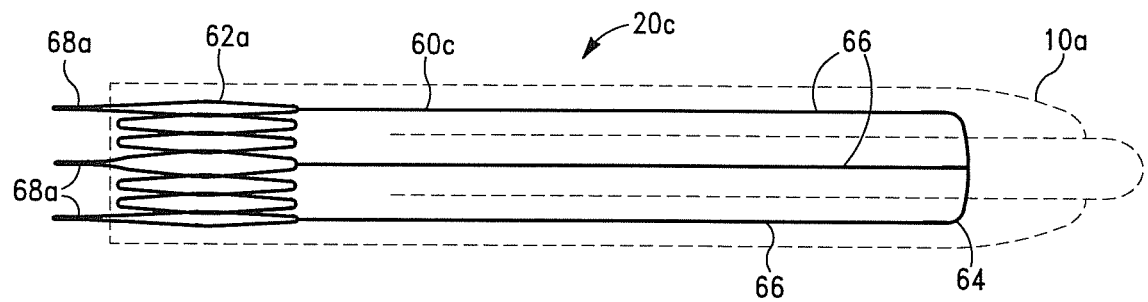
FIG. 9 is a side plan view of the prosthetic valve shown in FIG. 8A in a compressed pre-deployment configuration, in accordance with the invention.
Figure 10:
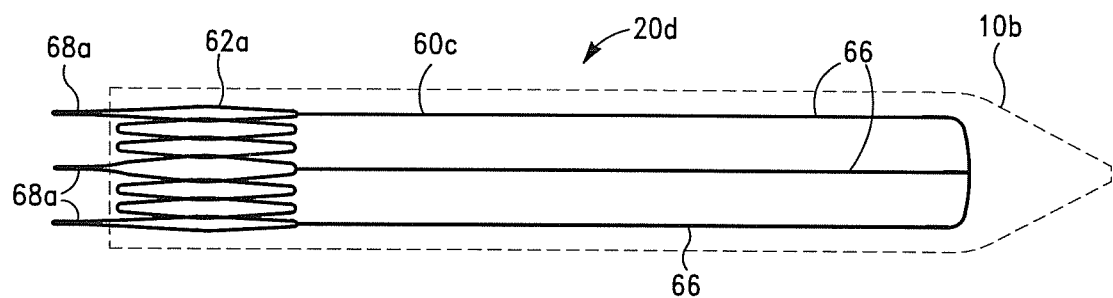
FIG. 10 is a side plan view of the prosthetic valve shown in FIG. 8B in a compressed pre-deployment configuration, in accordance with the invention.

As further set forth in Applicant's Co-pending U.S. application Ser. No. 17/233,890 and illustrated in FIGS. 9 and 10, the cross-linked wire structures 62a, 62b of stent structures 60a and 60b, respectively, are adapted to be compressed to a reduced size (i.e., diameter) tubular configuration to facilitate placement in and slidable translation through a percutaneous valve delivery apparatus or catheter assembly and, thereby, delivered therewith to a valve annulus, and, as indicated above, transition from the reduced size tubular configuration to an expanded post-deployment configuration, such as shown in FIGS. 8A and 8B.

As further set forth in Applicant's Co-pending U.S. application Ser. No. 17/233,890 the prosthetic valves 20c, 20d are further configured and adapted to (i) evert to an everted configuration, as illustrated by the everted configuration of prosthetic valve 20c shown in FIG. 11, and (ii) compress to a pre-deployment reduced size tubular configuration when in the everted configuration, as illustrated by the everted reduced size tubular configuration of prosthetic valve 20c shown in FIG. 12, to similarly facilitate placement in and translation through a percutaneous valve delivery apparatus or catheter assembly and, thereby, delivery therewith to a valve annulus, as described in detail below.

As indicated above, after the desired prosthetic valve of the invention is selected and provided (denoted step "i"), the second preferred step in the method for replacing a dysfunctional AV valve comprises providing a catheter assembly adapted to access the subject's heart, preferably, an AV valve annulus region of the dysfunctional AV valve to be replaced (denoted step "ii").

According to the invention, various conventional catheter assemblies that are adapted to access the subject's heart can be used to deliver a prosthetic valve of the invention to an AV valve annulus region. By way of example, one suitable catheter assembly is disclosed in U.S. Pat. No. 10,413,411.

For the sole purpose of describing a preferred catheter assembly and percutaneous transcatheter methods of the invention, prosthetic "ribbon structure" valve 20c shown in FIG. 8A will be selected for replacement of a dysfunctional AV valve. It is, however, to be understood that the catheter assembly described below and associated methods of the invention can also be readily employed to replace dysfunctional AV valves with any other prosthetic valve of the invention, including prosthetic "sheet structure" valves 20a and 20b, with stent structure 60a or 60b.

As indicated above, in many instances, the catheter assembly and percutaneous transcatheter method steps of the invention are described in connection with replacing a dysfunctional tricuspid valve. It is similarly to be understood that the catheter assembly and associated methods of the invention can also be readily employed to replace other dysfunctional AV valves, including, without limitation, dysfunctional mitral valves.

Figure 13:
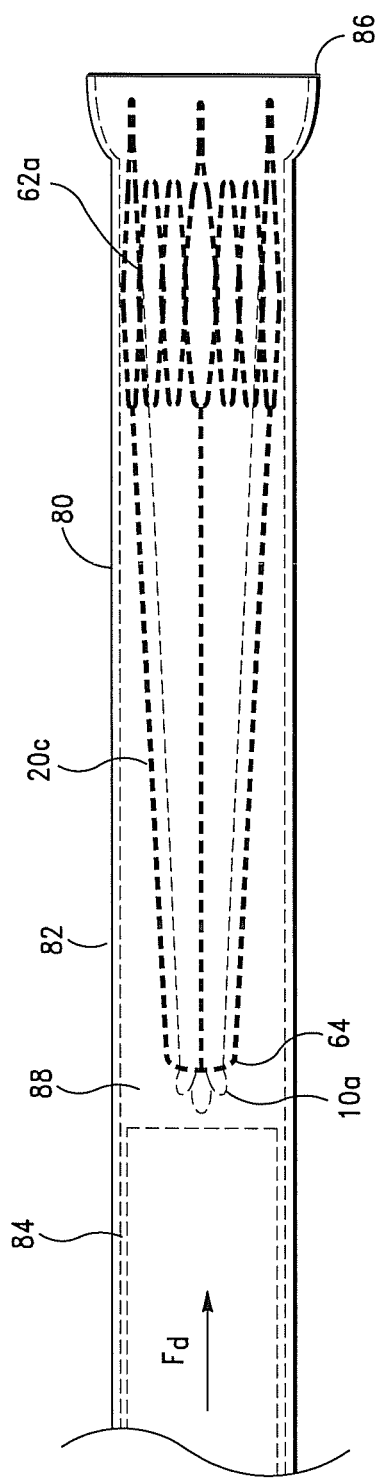
FIG. 13 is an illustration of one embodiment of a catheter assembly sheath member having the prosthetic valve shown in FIG. 8A disposed therein in an everted, compressed pre-deployment configuration, in accordance with the invention.
Figure 14:
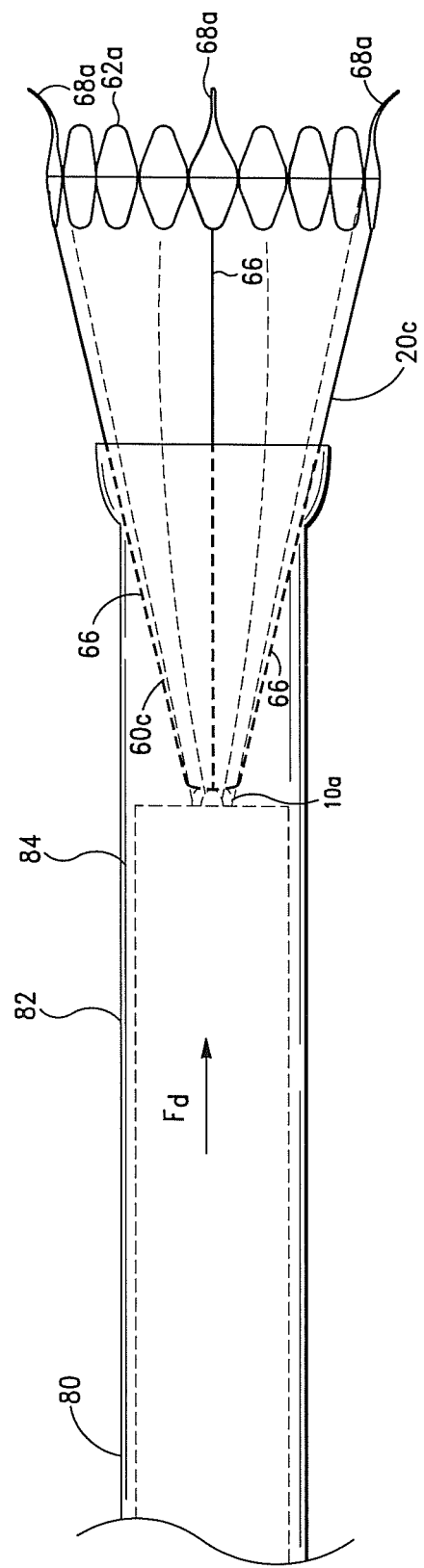
FIG. 14 is an illustration of the catheter assembly sheath member shown in FIG. 13 having the everted, compressed prosthetic valve shown in FIG. 8A partially disposed in and protruding out of the sheath member opening in an everted, partially expanded post-deployment configuration, in accordance with the invention.
Figure 15:
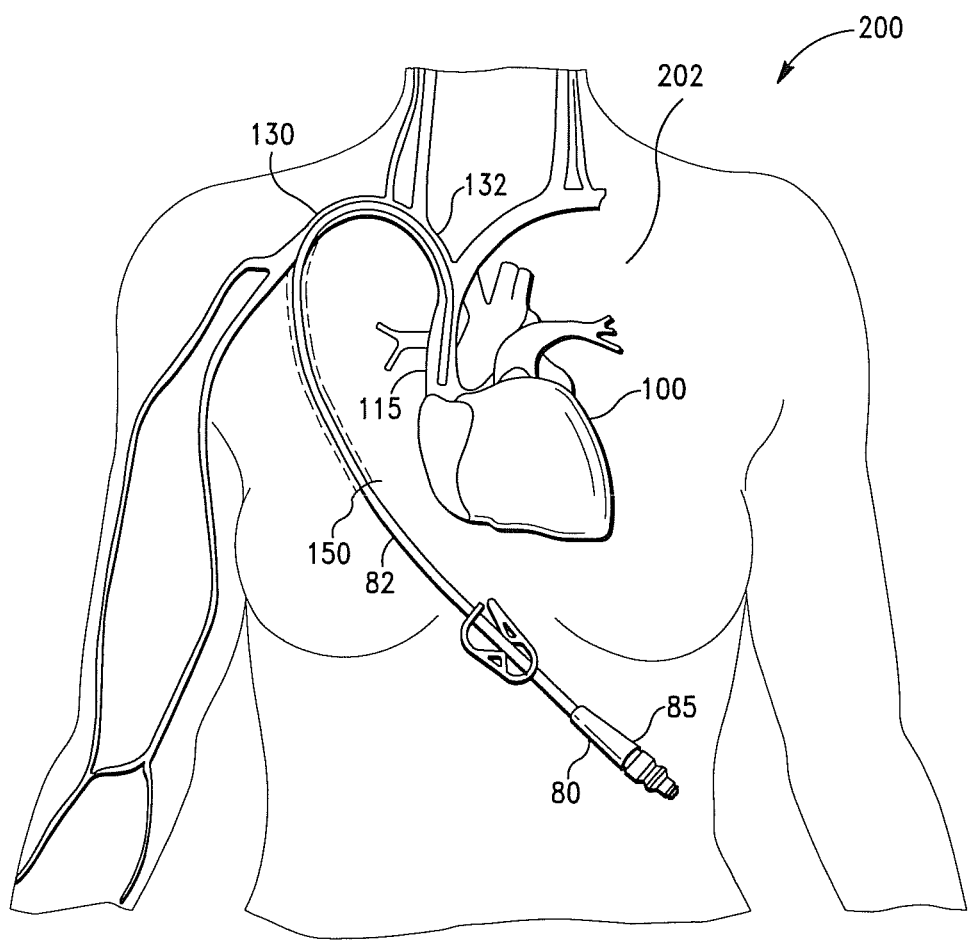
FIG. 15 is an illustration of a subject's chest region showing an incision proximate the right subclavian vein and a catheter sheath member inserted therethrough, in accordance with the invention.

Referring now to FIGS. 13-15, there are shown partial plan views of a catheter assembly 80, which can be employed to deliver a prosthetic valve of the invention in accordance with the methods of the invention.

As illustrated in FIGS. 13-15, the catheter assembly comprises a sheath member 82 comprising an internal lumen 88, a distal opening 86 and a deployment member 84 disposed in and adapted to be translated through the internal lumen 88.

According to the invention, the internal lumen 88 of the sheath member 82 is configured and adapted to receive a prosthetic valve of the invention therein, when in an everted, compressed pre-deployment configuration, such as illustrated in FIG. 13.

Referring now to FIG. 14, the deployment member 84 of the catheter assembly 80 is further configured and adapted to abut against and apply a force (denoted "$F_d$") to the circumferential distal end region 64 of expandable stent structure 60c and, thereby, distal end 54 of prosthetic valve 20c (and prosthetic valve 20d when disposed in the internal lumen 88 of the sheath member 82 in an everted, compressed pre-deployment configuration), whereby the prosthetic valve 20c is slidably translated through the internal lumen 88 and out of the sheath member distal opening 86.

Figure 16:
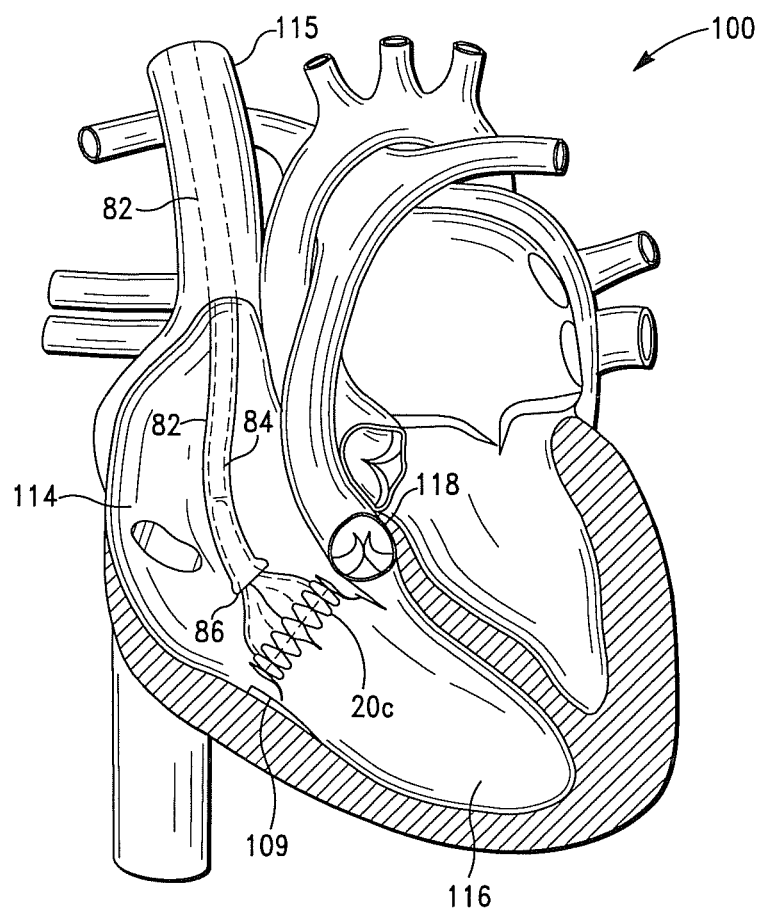
FIG. 16 is an illustration of a mammalian heart showing the deployment of the everted, expanded prosthetic valve shown in FIG. 8A to the tricuspid valve region of the heart with the catheter assembly sheath member shown in FIGS. 14 and 15, in accordance with the invention.

As illustrated in FIGS. 14 and 16, in a preferred embodiment, when the expandable stent structure 60c comprises Nitinol® (as set forth in Applicant's Co-pending U.S. application Ser. No. 17/233,890), as the prosthetic valve 20c slidably translates out of the sheath member distal opening 86, the cross-linked circumferential proximal end region 62a of the expandable stent structure 60c (and, thereby, open proximal annulus engagement end 52 of the prosthetic valve 20c) transitions from the everted, compressed, i.e., reduced size, pre-deployment configuration, shown in FIG. 12, to an everted, expanded configuration, such as shown in FIG. 14, and, ultimately, to an everted, fully expanded post-deployment configuration, such as shown in FIGS. 11 and 16.

Figure 11:
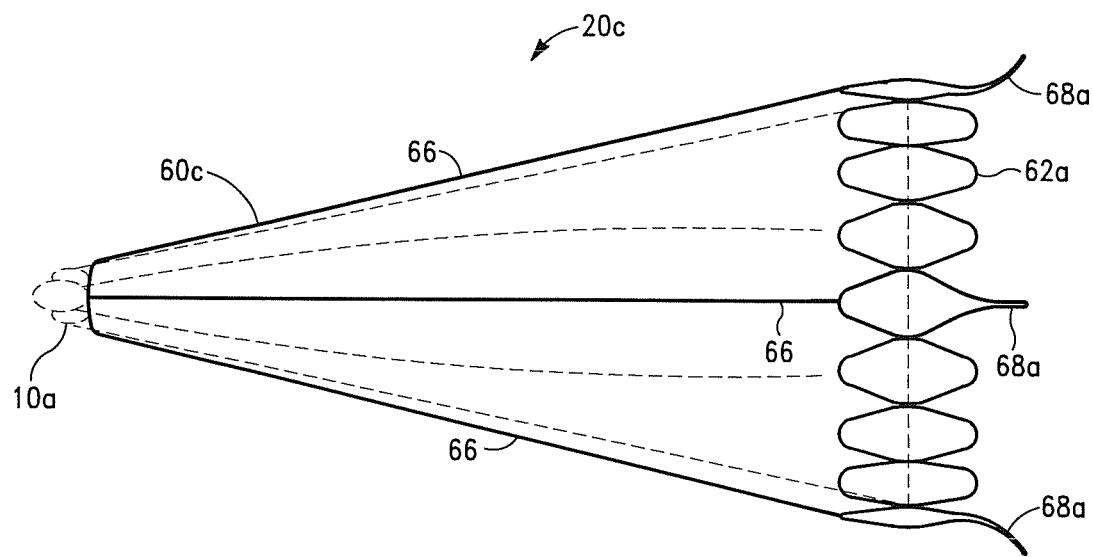
FIG. 11 is a perspective view of the prosthetic valve shown in FIG. 8A in an everted configuration, in accordance with the invention.

According to the invention, the transition of the cross-linked circumferential proximal end region 62a (and, thereby, open proximal annulus engagement end 52 of the prosthetic valve 20c) to the everted, expanded and fully expanded post-deployment configurations shown in FIGS. 11 and 16, respectively, is preferably achieved by virtue of the pre-crystal structure transformation temperature (denoted "Ar") physical characteristics of the stent material, i.e., Nitinol® and, thereby, stent structure 60c, e.g., modulus of elasticity, and the superelastic characteristics of the Nitinol® stent structure 60c when the stent structure 60c is subjected to a temperature greater than the crystal structure transformation temperature (Ar), e.g., core temperature of the recipient of prosthetic valve 20c.

As set forth in Applicant's Co-pending U.S. application Ser. No. 17/233,890, transition of the cross-linked circumferential proximal end region 62a of the expandable stent structure 60c (and, thereby, open proximal annulus engagement end 52 of the prosthetic valve 20c) to the everted, expanded and fully expanded post-deployment configurations shown in FIGS. 11 and 16, respectively, can also be achieved via the exertion of an internal radial force on the cross-linked wire structure 62a of the stent structure 60c (and, thereby, open proximal annulus engagement end 52 of the prosthetic valve 20c) by, for example, an expandable balloon component of a catheter assembly, e.g., a balloon catheter sub-assembly of the catheter assembly 80.

Figure 18:
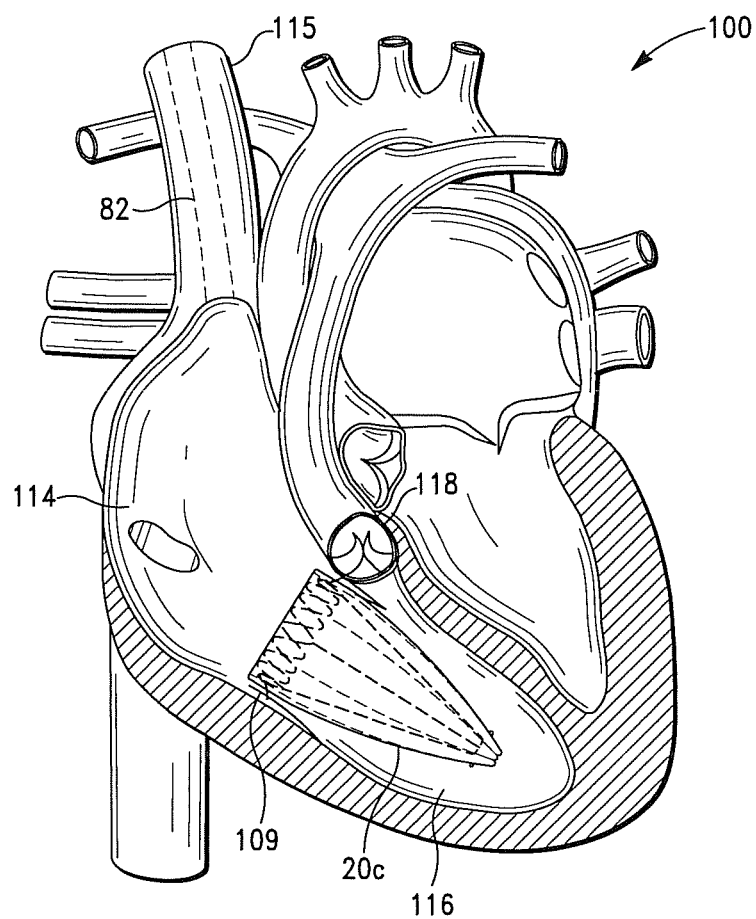
FIG. 18 is a further illustration of the mammalian heart shown in FIG. 16 showing the prosthetic valve shown in FIG. 8A engaged to the tricuspid valve region, in accordance with the invention.

In a preferred embodiment, the deployment member 84 of the catheter assembly 80 is further configured and adapted to continue applying force (Fa) to the circumferential distal end region 64 of stent structure 60c and, thereby, distal end of prosthetic valve 20c (and any other prosthetic valve of the invention, including prosthetic valve 20d) when the prosthetic valve 20c is engaged to an AV valve annulus, e.g., a tricuspid valve annulus, as shown in FIG. 16 and discussed in detail below, whereby the prosthetic valve 20c (and other prosthetic valves of the invention, including prosthetic valve 20d) is reverted to an expanded post-deployment configuration, as shown in FIG. 18.

As further indicated above, after the catheter assembly is provided (denoted method step "ii"), the third preferred step in the method for replacing a dysfunctional AV valve of the invention comprises everting the provided prosthetic valve to an everted pre-deployment configuration (denoted method step "iii"), in this instance, everting prosthetic valve 20c to an everted pre-deployment configuration, such as shown in FIG. 11.

Figure 12:
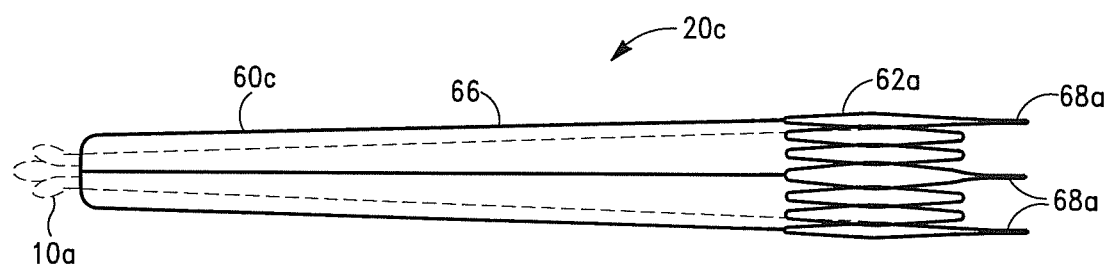
FIG. 12 is a perspective partial sectional view of the prosthetic valve shown in FIG. 8A in an everted, compressed pre-deployment configuration, in accordance with the invention.

After the prosthetic valve is everted to the everted pre-deployment configuration, the prosthetic valve, in this instance, prosthetic valve 20c, is compressed to an everted, compressed pre-deployment configuration, such as shown in FIG. 12 (denoted method step "iv").

After the prosthetic valve is compressed to the everted, compressed pre-deployment configuration, the everted, compressed prosthetic valve, in this instance, prosthetic valve 20c, is loaded or positioned in the catheter assembly sheath member 82 (denoted method step "v").

After the prosthetic valve, in this instance, prosthetic valve 20c, is loaded into the sheath member 82, a vein is selected that provides access to the subject's heart 100, more preferably, the AV valve annulus of the dysfunctional AV valve (denoted method step "vi").

According to the invention, various veins and tributaries thereof can be employed to access the subject's heart 100, e.g., jugular vein, subclavian vein, femoral vein, popliteal vein and great saphenous vein.

When the dysfunctional AV valve to be replaced comprises a dysfunctional tricuspid valve, a subclavian vein is preferably employed to access the subject's heart.

When the dysfunctional AV valve to be replaced comprises a dysfunctional mitral valve, a popliteal vein is preferably employed to access the subject's heart.

Referring now to FIG. 15, after the vein is selected, in this instance, the right subclavian vein 130, an incision 150 is placed in and through the tissue in the chest region 202 of subject 200 proximate the right subclavian vein 130 (denoted method step "vii") to provide access therein by the catheter assembly 80.

After the incision is placed in and through the tissue in the chest region 202 of subject 200 proximate the right subclavian vein 130, the sheath member 82 of catheter assembly 80 is routed into the incision 150 and into the subject's heart 100 (denoted method step "viii"), in this instance, the right atrium 114 of the subject's heart 100; preferably, into and through the right brachiocephalic vein 132, into and through the superior vena cava 115 and into the right atrium 114.

As illustrated in FIG. 15, the control unit 85 of the catheter assembly 80 preferably remains outside of the body of subject 200 and is accessible by an operator, e.g., a surgeon.

According to the invention, after the sheath member 82 is routed into the subject's heart 100, the sheath member 82 is guided into the AV valve annulus of the dysfunctional AV valve (denoted method step "ix"), in this instance, the tricuspid valve region 109 of the subject's heart 100.

As illustrated in FIG. 16, after the sheath member 82 is guided into the subject's heart 100, in this instance, the tricuspid valve region 109 of the subject's heart 100, the everted, compressed prosthetic valve is slidably translated out of the catheter assembly sheath member 82 and into the AV valve annulus region of the dysfunctional AV valve (denoted method step "x"), again, in this instance, the tricuspid valve region 109 of the subject's heart 100, wherein, according to the invention, the prosthetic valve transitions from the everted, compressed pre-deployment configuration to the everted, expanded post-deployment configuration, whereby the prosthetic valve 20c is disposed proximate the cardiovascular tissue of the tricuspid valve annulus region 109 and the plurality of stent tethers 68a pierce into cardiovascular tissue at the tricuspid valve region 109 and, thereby, position the everted, expanded prosthetic valve 20c at the tricuspid valve region 109 and securely engage the everted, expanded prosthetic valve 20c thereto.

Figure 17:
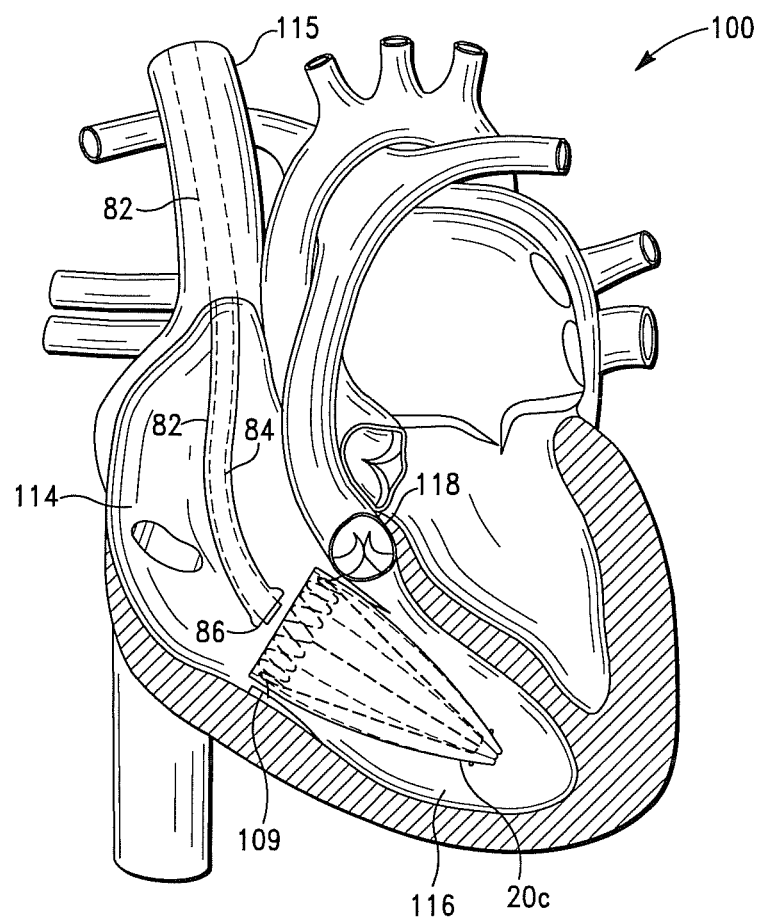
FIG. 17 is a further illustration of the mammalian heart shown in FIG. 16 showing the catheter assembly sheath member shown in FIG. 16 and the reverted, expanded prosthetic valve shown in FIG. 8A disposed in the tricuspid valve region of the heart, in accordance with the invention.

Referring now to FIG. 17, after the prosthetic valve, in this instance, prosthetic valve 20c, is slidably translated out of the distal opening 86 of sheath member 82 and into the AV valve annulus region of the dysfunctional AV valve, whereby the stent tethers 68a engage the AV valve annulus region, the prosthetic valve 20c is reverted to an expanded post-deployment configuration (denoted method step "xi").

As indicated above, in a preferred embodiment, the prosthetic valve is reverted to the expanded post-deployment configuration by a force ($F_d$) that is exerted on the circumferential distal end region 64 of stent structure 60c and, thereby, distal end of the prosthetic valve 20c by the deployment member 84 of the catheter assembly 80.

After the prosthetic valve, in this instance, prosthetic valve 20c, is reverted to the expanded post-deployment configuration, the sheath member 82 of the catheter assembly 80 is withdrawn from the heart 100, as shown in FIG. 18, and out of the subject's body 200 (denoted method step "xii").

In accordance with the invention, there is thus provided at least one embodiment of a method for replacing a dysfunctional tricuspid valve comprising the steps of:
  (i) providing a prosthetic valve of the invention, the prosthetic valve comprising a base valve structure and a self-expanding stent structure,
  the stent structure comprising a shape-memory alloy and a plurality of tethers adapted to pierce cardiovascular tissue and engage the base valve structure thereto,
  the prosthetic valve being adapted to be everted to an everted pre-deployment configuration and, thereafter, be compressed to an everted, compressed pre-deployment configuration,
  the prosthetic valve being further adapted to transition from the everted, compressed pre-deployment configuration to an everted, expanded post-deployment configuration, and, thereafter, be reverted to a reverted, expanded post-deployment configuration;
  (ii) providing a catheter assembly adapted to access the tricuspid valve annulus region of the dysfunctional tricuspid valve,
  the catheter assembly comprising a sheath member and a deployment member, the sheath member comprising an internal lumen and a distal opening,
  the internal lumen of the sheath member being adapted to receive the prosthetic valve therein when the prosthetic valve is in the everted, compressed pre-deployment configuration,
  the deployment member being adapted to be translated through the internal lumen;
  (iii) everting the prosthetic valve to the everted pre-deployment configuration;
  (iv) compressing the prosthetic valve in the everted pre-deployment configuration to the everted, compressed pre-deployment configuration;
  (v) loading the prosthetic valve in the everted, compressed pre-deployment configuration into the sheath member internal lumen;
  (vi) selecting a vein that provides access to the tricuspid valve annulus region of the dysfunctional tricuspid valve;
  (vii) placing an incision through tissue proximate the vein and through the vein, wherein an opening is provided in the vein;
  (viii) inserting the catheter assembly sheath member through the incision and into and through the vein, and into the right atrium of the subject's heart;
  (ix) guiding the catheter assembly sheath member into the tricuspid valve annulus region of the dysfunctional tricuspid valve;
  (x) slidably translating the prosthetic valve in the everted, compressed pre-deployment configuration through the sheath member internal lumen, out of the distal opening of the sheath member and into the tricuspid valve annulus region of the dysfunctional tricuspid valve with the deployment member, wherein the prosthetic valve transitions from the everted, compressed pre-deployment configuration to the everted, expanded post-deployment configuration, whereby the plurality of stent structure tethers pierce into the cardiovascular tissue at the tricuspid valve annulus region and, thereby, position the prosthetic valve at the tricuspid valve annulus region and securely engage the prosthetic valve thereto in the everted, expanded post-deployment configuration;

(xi) reverting the prosthetic valve in the everted, expanded post-deployment configuration to the reverted, expanded post-deployment configuration; and (xii) withdrawing the sheath member of the catheter assembly out of the right atrium of the subject's heart and out of the subject's body.

In accordance with the invention, there is also provided at least one embodiment of a method for replacing a dysfunctional mitral valve comprising the steps of:

(i) providing a prosthetic valve of the invention, the prosthetic valve comprising a base valve structure and a self-expanding stent structure, the stent structure comprising a shape-memory alloy and a plurality of tethers adapted to pierce cardiovascular tissue and engage the base valve structure thereto, the prosthetic valve being adapted to be everted to an everted pre-deployment configuration and, thereafter, be compressed to an everted, compressed pre-deployment configuration, the prosthetic valve being further adapted to transition from the everted, compressed pre-deployment configuration to an everted, expanded post-deployment configuration, and, thereafter, be reverted to a reverted, expanded post-deployment configuration;

(ii) providing a catheter assembly adapted to access the mitral valve annulus region of the dysfunctional mitral valve, the catheter assembly comprising a sheath member and a deployment member, the sheath member comprising an internal lumen and a distal opening, the internal lumen of the sheath member being adapted to receive the prosthetic valve therein when the prosthetic valve is in the everted, compressed pre-deployment configuration, the deployment member being adapted to be translated through the internal lumen;

(iii) everting the prosthetic valve to the everted pre-deployment configuration;

(iv) compressing the prosthetic valve in the everted pre-deployment configuration to the everted, compressed pre-deployment configuration;

(v) loading the prosthetic valve in the everted, compressed pre-deployment configuration into the sheath member internal lumen;

(vi) selecting a vein, preferably, a popliteal vein, that provides access to the mitral valve annulus region of the dysfunctional mitral valve;

(vii) placing an incision through tissue proximate the vein and through the vein, wherein an opening is provided in the vein;

(viii) inserting the catheter assembly sheath member through the incision and into and through the vein, and into the right atrium of the subject's heart;

(ix) guiding the catheter assembly sheath member into and through a preformed opening of the atrial septum of the subject's heart and into the left atrium of the subject's heart;

(x) guiding the catheter assembly sheath member into the mitral valve annulus region of the dysfunctional mitral valve;

(xi) slidably translating the prosthetic valve in the everted, compressed pre-deployment configuration through the sheath member internal lumen, out of the distal opening of the sheath member and into the mitral valve annulus region of the dysfunctional mitral valve with the deployment member, wherein the prosthetic valve transitions from the everted, compressed pre-deployment configuration to the everted, expanded post-deployment configuration, whereby the plurality of stent structure tethers pierce into the cardiovascular tissue at the mitral valve annulus region and, thereby, position the prosthetic valve at the mitral valve annulus region and securely engage the prosthetic valve thereto in the everted, expanded post-deployment configuration;

(xii) reverting the prosthetic valve in the everted, expanded post-deployment configuration to the reverted, expanded post-deployment configuration; and (xiii) withdrawing the sheath member of the catheter assembly out of the left atrium of the subject's heart and out of the subject's body.

In some embodiments of the invention, there is further provided a method for replacing a dysfunctional AV valve comprising:

(i) providing a prosthetic valve of the invention, the prosthetic valve comprising a base valve structure and a self-expanding stent structure, the prosthetic valve being adapted to be everted to an everted pre-deployment configuration and, thereafter, be compressed to an everted, compressed pre-deployment configuration, the prosthetic valve being further adapted to transition from the everted, compressed pre-deployment configuration to an everted, expanded post-deployment configuration, and, thereafter, be reverted to a reverted, expanded post-deployment configuration;

(ii) providing a catheter assembly adapted to access the AV valve annulus region of the dysfunctional AV valve, the catheter assembly comprising a sheath member, a deployment member and an intra-cardiac suturing device, the sheath member comprising an internal lumen and a distal opening, the internal lumen of the sheath member being adapted to receive the prosthetic valve therein when the prosthetic valve is in the everted, compressed pre-deployment configuration, the deployment member being adapted to be translated through the internal lumen;

(iii) everting the prosthetic valve to the everted pre-deployment configuration;

(iv) compressing the prosthetic valve in the everted pre-deployment configuration to the everted, compressed pre-deployment configuration;

(v) loading the prosthetic valve in the everted, compressed pre-deployment configuration into the sheath member internal lumen;

(vi) selecting a vein that provides access to the AV valve annulus region of the dysfunctional AV valve;

(vii) placing an incision through tissue proximate the vein and through the vein, wherein an opening is provided in the vein;

(viii) inserting the catheter assembly sheath member through the incision and into and through the vein, and into the subject's heart;

(ix) guiding the catheter assembly sheath member to the AV valve annulus region of the dysfunctional AV valve;

(x) slidably translating the prosthetic valve in the everted, compressed pre-deployment configuration through the sheath member internal lumen, out of the distal opening of the sheath member and into the AV valve annulus region of the dysfunctional AV valve with the deployment member, wherein the prosthetic valve transitions from the everted, compressed pre-deployment configuration to the everted, expanded post-deployment configuration, whereby the prosthetic valve is disposed proximate the cardiovascular tissue of the AV valve annulus region of the dysfunctional AV valve;

(xi) suturing the prosthetic valve in the everted, compressed pre-deployment configuration to the AV valve annulus region with the intra-cardiac suturing device;

(xii) reverting the prosthetic valve in the everted, expanded post-deployment configuration to the reverted, expanded post-deployment configuration; and (xiii) withdrawing the sheath member of the catheter assembly out of the subject's body.

In embodiments of the invention, wherein the dysfunctional AV valve comprises a dysfunctional tricuspid valve, the noted method steps are similar, except for the following: (i) the AV valve annulus region comprises a tricuspid valve annulus region, the vein selected provides access to the tricuspid valve annulus region of the dysfunctional tricuspid valve, and the catheter assembly sheath member is preferably guided into the right atrium of the subject's heart.

In embodiments of the invention, wherein the dysfunctional valve comprises a dysfunctional mitral valve, the noted method steps are similar, except for the following: (i) the AV valve annulus comprises a mitral valve annulus region, the vein selected provides access to the mitral valve annulus region of the dysfunctional mitral valve, and the catheter assembly sheath member is preferably guided into the left atrium of the subject's heart through a preformed opening of the atrial septum.

According to the invention, in some embodiments, the open proximal engagement end of the prosthetic valves of the invention, i.e., base valve structure thereof, can further include an outer coating comprising a poly(glycerol sebacate) (PGS) based adhesive composition, such as disclosed in Applicant's Co-pending U.S. application Ser. No. 17/231,784, which is expressly incorporated by reference herein.

In such embodiments, the noted proximal valves can be employed to replace dysfunctional AV valves via the aforedescribed method with the exception of the following: after slidably translating the prosthetic valve in the everted, compressed pre-deployment configuration through the sheath member internal lumen, out of the distal opening of the sheath member and into the AV valve annulus region of the dysfunctional AV valve with the deployment member, wherein the prosthetic valve transitions from the everted, compressed pre-deployment configuration to the everted, expanded post-deployment configuration, whereby the prosthetic valve is disposed proximate the cardiovascular tissue of the AV valve annulus region of the dysfunctional AV valve (i.e., method step "x"), instead of suturing the prosthetic valve in the everted, compressed pre-deployment configuration to the AV valve annulus region with the intra-cardiac suturing device, light or thermal energy is delivered to the coated open proximal engagement end of the prosthetic valve, whereby, as described in detail in Co-pending U.S. application Ser. No. 17/231,784, the PGS component in the PGS based composition cures (or is activated) and the coated open proximal engagement end of the prosthetic valve adheres to the AV valve annulus region of the dysfunctional AV valve.

As further set forth in Applicant's Co-pending U.S. application Ser. No. 17/233,890, the prosthetic valves can also comprise a stent structure that does not comprise a shape-memory alloy, e.g., stainless steel.

In such embodiments of the invention, there is also provided a method for replacing a dysfunctional AV valve comprising:

(i) providing a prosthetic valve of the invention, the prosthetic valve comprising a base valve structure and a stent structure, the prosthetic valve being adapted to be everted to an everted pre-deployment configuration and, thereafter, be compressed to an everted, compressed pre-deployment configuration, the prosthetic valve being further adapted to transition from the everted, compressed pre-deployment configuration to an everted, expanded post-deployment configuration, and, thereafter, be reverted to a reverted, expanded post-deployment configuration;

(ii) providing a catheter assembly adapted to access the AV valve annulus region of the dysfunctional AV valve, the catheter assembly comprising a sheath member, a deployment member and an expandable balloon device, the sheath member comprising an internal lumen and a distal opening, the internal lumen of the sheath member being adapted to receive the prosthetic valve therein when the prosthetic valve is in the everted, compressed pre-deployment configuration, the deployment member being adapted to be translated through the internal lumen;

(iii) everting the prosthetic valve to the everted pre-deployment configuration;

(iv) compressing the prosthetic valve in the everted pre-deployment configuration to the everted, compressed pre-deployment configuration;

(v) loading the prosthetic valve in the everted, compressed pre-deployment configuration into the sheath member internal lumen;

(vi) selecting a vein that provides access to the AV valve annulus region of the dysfunctional AV valve;

(vii) placing an incision through tissue proximate the vein and through the vein, wherein an opening is provided in the vein;

(viii) inserting the catheter assembly sheath member through the incision and into and through the vein, and into the subject's heart;

(ix) guiding the catheter assembly sheath member to the AV valve annulus region of the dysfunctional AV valve;

(x) slidably translating the prosthetic valve in the everted, compressed pre-deployment configuration through the sheath member internal lumen, out of the distal opening of the sheath member and into the AV valve annulus region of the dysfunctional AV valve with the deployment member;

(xi) expanding the stent structure and, thereby, open proximal end of the prosthetic valve with the expandable balloon device, wherein the prosthetic valve is placed in the everted, expanded post-deployment configuration, whereby the prosthetic valve is disposed proximate the cardiovascular tissue of the AV valve annulus region of the dysfunctional AV valve;

(xii) reverting the prosthetic valve in the everted, expanded post-deployment configuration to the reverted, expanded post-deployment configuration; and (xiii) withdrawing the sheath member of the catheter assembly out of the subject's body.

In a preferred embodiment, the prosthetic valves of the invention are delivered to the AV valve annulus of the dysfunctional AV valve with the methods of the invention described herein proximate the region (or position) of the dysfunctional AV valve.

According to the invention, the prosthetic valves of the invention can be delivered to the same position on the AV valve annulus as the dysfunctional AV valve to be replaced with the methods of the invention.

As indicated above, a seminal advantage of the methods of the invention is that the prosthetic valves of the invention can be delivered proximate to a region proximate to or at the same position of the dysfunctional AV valve to be replaced without removing the dysfunctional AV valve or leaflets thereof.

According to the invention, the methods for replacing a dysfunctional AV valve described herein can also be readily employed to replace dysfunctional AV valves with prosthetic valves disclosed in Applicant's U.S. Pat. Nos. 10,188,510, 9,044,319, 8,709,076, 9,011,526, 9,308,084, 9,907,649, 8,790,397, 8,845,719 and 8,696,744, and U.S. application Ser. Nos. 16/440,504, 17/177,359, 17/178,562 and 17/181,161.

In some embodiments of the invention, during the methods for replacing a dysfunctional AV valve described above, a rapid heart rate is induced, wherein blood flow to and through the dysfunctional AV valve to be replace is reduced, more preferably, abated.

In some embodiments of the invention, the induced heart rate is in the range of approximately 200-300 beats/min., more preferably, approximately 250 beats/min.

In some embodiments, the rapid heart rate is induced for a period of time greater than 5 seconds, more preferably, in the range of 5-20 seconds.

As will readily be appreciated by one having ordinary skill in the art, the percutaneous transcatheter valve delivery methods of the invention provide numerous advantages over conventional transcatheter valve delivery methods. Among the advantages are the following:

The provision of percutaneous transcatheter valve delivery methods that provide a highly effective means for positioning and securing prosthetic valves to AV valve annuli;

The provision of percutaneous transcatheter valve delivery methods for replacing dysfunctional AV valves that (i) accurately position replacement prosthetic valves in an AV valve annulus region and (ii) facilitate secure and reliable engagement of the prosthetic valves to the AV valve annulus region;

The provision of percutaneous transcatheter valve delivery methods for replacing dysfunctional AV valves that do not require the removal of native dysfunctional AV valves or leaflets thereof prior to replacement with a prosthetic valve.

The provision of percutaneous transcatheter valve delivery methods for replacing dysfunctional AV valves that position a prosthetic "tricuspid" valve in a tricuspid valve region, whereby the prosthetic "tricuspid" valve does not obstruct the outflow tract of the adjacent pulmonary valve and prevents the leaflets of the pulmonary valve from coapting; and The provision of percutaneous transcatheter valve delivery methods for replacing dysfunctional AV valves that position a prosthetic "mitral" valve in a mitral valve region, whereby the prosthetic "mitral" valve does not obstruct the outflow tract of the adjacent aortic valve and prevents the leaflets of the aortic valve from coapting.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method for replacing a dysfunctional atrioventricular (AV) valve in a heart of a subject, comprising the steps of:
   (i) providing a prosthetic valve, said prosthetic valve comprising a base valve structure and a self-expanding stent structure,
   said base valve structure comprising collagenous tissue derived from a first mammalian tissue source,
   said base valve structure further comprising an internal region, an open proximal valve annulus engagement end and a distal valve structure end, said open proximal valve annulus engagement end being configured and adapted to engage an AV valve annulus, receive fluid flow therein and direct said fluid flow into said internal region of said base valve structure,
   said base valve structure further comprising a plurality of elongated ribbon members that extend from said open proximal valve annulus engagement end to said distal valve structure end, each of said plurality of elongated ribbon members comprising first and second edge regions and proximal and distal ends, said plurality of elongated ribbon members being positioned circumferentially about said base valve structure, wherein said first edge regions of said plurality of elongated ribbon members are positioned proximate said second edge regions of said plurality of elongated ribbon members and form a plurality of flow modulating regions,
   said distal ends of said plurality of elongated ribbon members being positioned proximate each other in a constrained relationship, wherein said fluid flow through said distal ends of said plurality of elongated ribbon members and, thereby, said base valve structure is restricted,
   said plurality of elongated ribbon members being configured and adapted to deflect outwardly when said open proximal valve annulus engagement end of said base valve structure directs said fluid flow into said internal region of said base valve structure and said fluid flow comprises a positive fluid pressure, whereby a first pressure differential between first valvular pressure in said internal region of said base valve structure relative to first external pressure exerted on said base valve structure is generated, wherein each of said plurality of flow modulating regions transitions from a restricted fluid flow configuration to an open fluid flow configuration and allows said fluid flow to be transmitted through said plurality of flow modulating regions and, thereby, through and out of said base valve structure,
   said plurality of elongated ribbon members being further configured and adapted to deflect inwardly when said first pressure differential transitions to a second pressure differential between second valvular pressure in said internal region of said base valve structure relative to second external pressure exerted on said base valve structure, said second pressure differential being lower than said first pressure differential, wherein each of said plurality of flow modulating regions transitions from said open fluid flow configuration to said restricted fluid flow configuration and restricts said fluid flow through said plurality of flow modulating regions and, thereby, through and out of said base valve structure, said self-expanding stent structure being positioned in said internal region of said base valve structure, said self-expanding stent structure comprising a shape-memory alloy, said self-expanding stent structure comprising a plurality of tethers adapted to pierce into and engage cardiovascular tissue, said prosthetic valve being adapted to be everted to an everted pre-deployment configuration and, thereafter, be compressed to an everted, compressed pre-deployment configuration, said prosthetic valve being further adapted to transition from said everted, compressed pre-deployment configuration to an everted, expanded post-deployment configuration, and, thereafter, be reverted to a reverted, expanded post-deployment configuration;

(ii) providing a catheter assembly adapted to access an AV valve annulus region of said dysfunctional AV valve, said catheter assembly comprising a sheath member and a deployment member, said sheath member comprising an internal lumen and a distal opening, said internal lumen of said sheath member being adapted to receive said prosthetic valve therein when said prosthetic valve is in said everted, compressed pre-deployment configuration, said deployment member being adapted to be translated through said internal lumen;

(iii) everting said prosthetic valve to said everted pre-deployment configuration;

(iv) compressing said prosthetic valve in said everted pre-deployment configuration to said everted, compressed pre-deployment configuration;

(v) loading said prosthetic valve in said everted, compressed pre-deployment configuration into said internal lumen of said sheath member of said catheter assembly;

(vi) selecting a vein in communication with said heart of said subject, said vein providing access to said AV valve annulus region of said dysfunctional AV valve;

(vii) placing an incision through tissue proximate said vein and through said vein, wherein an opening is provided in said vein;

(viii) inserting said sheath member of said catheter assembly through said incision and A into and through said vein, and into said heart of said subject;

(ix) guiding said sheath member of said catheter assembly into said AV valve annulus region of said dysfunctional AV valve;

(x) slidably translating said prosthetic valve in said everted, compressed pre-deployment configuration through said internal lumen of said sheath member, out of said distal opening of said sheath member and into said AV valve annulus region of said dysfunctional AV valve with said deployment member, wherein said prosthetic valve transitions from said everted, compressed pre-deployment configuration to said everted expanded post-deployment configuration, whereby said plurality of tethers of said self-expanding stent structure pierce into said cardiovascular tissue at said AV valve of said dysfunctional AV valve and, thereby, position said prosthetic valve at said AV valve of said dysfunctional AV valve and securely engage said prosthetic valve thereto in said everted, expanded post-deployment configuration;

(xi) reverting said prosthetic valve in said everted, expanded post-deployment configuration to said reverted, expanded post-deployment configuration; and (xii) withdrawing said sheath member of said catheter assembly out of said subject's body.

2. The method of claim 1, wherein said first mammalian tissue source is selected from the group consisting of the heart, small intestine, large intestine, stomach, lung, liver, kidney, pancreas, peritoneum, placenta, amniotic membrane, umbilical cord, bladder, prostate, and fetal tissue from any mammalian organ.

3. The method of claim 1, wherein said first mammalian tissue source is devoid of xenogeneic antigens.

4. The method of claim 1, wherein said collagenous tissue comprises a first pharmacological agent.

5. The method of claim 4, wherein said first pharmacological agent is selected from the group consisting of an antibiotic, anti-viral agent, analgesic, anti-inflammatory, anti-neoplastic, anti-spasmodic, anticoagulant and anti-thrombotic.

6. The method of claim 5, wherein said antibiotic is selected from the group consisting of aminoglycosides, cephalosporins, chloramphenicol, clindamycin, erythromycins, fluoroquinolones, macrolides, azolides, metronidazole, penicillin, tetracyclines, trimethoprim-sulfamethoxazole, gentamicin and vancomycin.

7. The method of claim 5, wherein said anti-inflammatory is selected from the group consisting of dexamethasone, betamethasone and prednisolone.

8. The method of claim 1, wherein said shape-memory alloy comprises a nickel-titanium (Ni—Ti) alloy.

9. The method of claim 1, wherein said self-expanding stent structure comprises an outer coating.

10. The method of claim 9, wherein said outer coating comprises an extracellular matrix (ECM) composition comprising acellular ECM derived from a second mammalian tissue source.

11. The method of claim 10, wherein said second mammalian tissue source is selected from the group consisting of small intestine submucosa (SIS), urinary bladder submucosa (UBS), stomach submucosa (SS), heart tissue, mesothelial tissue, placental tissue and omentum tissue.

12. The method of claim 10, wherein said ECM composition is in the form of an expandable composition.

13. The method of claim 10, wherein said ECM composition further comprises a second pharmacological agent selected from the group consisting of dexamethasone, betamethasone and prednisolone.

* * * * *